US005086187A

United States Patent [19]

Anderson-McKay et al.

[11] Patent Number: 5,086,187

[45] Date of Patent: Feb. 4, 1992

[54] HERBICIDAL PYRONES

[75] Inventors: Janet E. Anderson-McKay, Newtown; Andris J. Liepa, Wheelers Hill, both of Australia

[73] Assignee: Dunlena Pty. Limited, North Sydney, Australia

[21] Appl. No.: 531,325

[22] Filed: May 31, 1990

Related U.S. Application Data

[62] Division of Ser. No. 188,800, Apr. 13, 1988, Pat. No. 4,939,278.

[51] Int. Cl.[5] .................... C07D 337/02; C07D 311/96

[52] U.S. Cl. .......................................... 549/9; 549/11; 549/13; 549/20; 549/29; 549/35; 549/265; 71/81; 71/88; 71/90

[58] Field of Search ....................... 549/265, 9, 11, 13, 549/20, 29, 35; 71/81, 88, 90

[56] References Cited

U.S. PATENT DOCUMENTS

| | | | |
|---|---|---|---|
| 3,950,420 | 4/1976 | Sawaki et al. | 260/563 |
| 4,008,067 | 2/1977 | Hirono | 71/88 |
| 4,011,256 | 3/1977 | Sawaki et al. | 260/468 J |
| 4,075,239 | 2/1978 | Sawaki et al. | 260/464 |

FOREIGN PATENT DOCUMENTS

| | | |
|---|---|---|
| 71829/74 | 9/1975 | Australia . |
| 35314/78 | 9/1979 | Australia . |
| 2140803 | 12/1984 | United Kingdom . |

OTHER PUBLICATIONS

Chemical Abstracts, 86:72439y.
Chemical Abstracts, 102:184973y.

*Primary Examiner*—C. Warren Ivy
*Assistant Examiner*—Ba K. Trinh
*Attorney, Agent, or Firm*—James A. Costello

[57] ABSTRACT

Compounds of the general formula, including isomers and tautomers thereof:

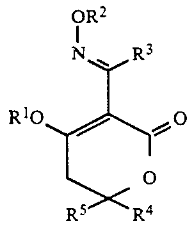

wherein:

$R^1$ to $R^5$ are as defined in the text; the compounds have herbicidal and plant growth regulating properties; including compositions containing them, methods for using them and intermediates for making them.

11 Claims, No Drawings

HERBICIDAL PYRONES

This is a division of application Ser. No. 188,800, filed Apr. 13, 1988, now U.S. Pat. No. 4,939,278.

This invention relates to organic compounds having herbicidal properties and plant growth regulating properties, to processes for the preparation of such compounds; to intermediates useful in the preparation of such compounds; to herbicidal compositions and processes utilizing such compounds and to plant growth regulating compositions and processes utilizing such compounds.

The use of certain cyclohexane-1,3-dione derivatives as grass herbicides is known in the art. Thus, for example, the compendium "Agricultural Chemicals-Book II Herbicides 1986-87 Revision" (W. T. Thomson Editor, Thomson Publications, California U.S.A.) describes the cyclohexane-1,3-dione derivatives known commercially as Alloxydim Sodium (methyl-3-[1-(allyloxyimino)butyl]-4-hydroxy-6,6-dimethyl-2-oxocyclohex-3-ene carboxylate), Cloproxydim ((E,E)-2[1-[1-[(3-chloro-2-propenyl)oxy]imino]butyl]-5-[2-(ethylthio)-propyl]-3-hydroxy-2-cyclohexen-1-one), Cycloxydim (2-[1-ethoxyimino)butyl]-3-hydroxy-5-[2H-tetrahydro-thiopyran-3-yl]-2-cyclohexen-1-one and Sethoxydim (2-[1-(ethoxyimino)butyl[-5-[2-ethxylthio]propyl-3-hydroxy-2-cyclohexen-1-one) as selective post-emergent herbicides. Alloxydim and Sethoxydim have been disclosed in Australian Patent No. 464 655 and Australian Patent Application No. 35,314/78 respectively.

Pyrones of the general Formula (1) have been claimed to show herbicidal activity (Japan Kokai 76 63175 (*Chemical Abstracts,* 86:72439y)).

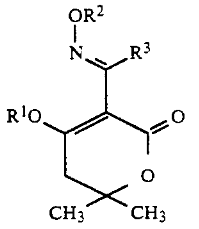

(1)

We have discovered that compounds similar to the general Formula (1) but which bear substituents at the 6-position other than hydrogen or geminal dimethyl exhibit particularly useful herbicidal activity, with special selectivity for weed grasses in crops, and plant growth regulating activity.

Accordingly, the invention provides a compound of the general Formula (2)

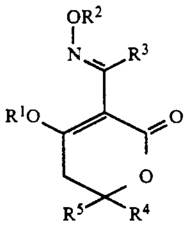

(2)

wherein $R^1$ is selected from the group consisting of: hydrogen; alkyl; alkenyl; alkynyl; cycloalkyl; cycloalkenyl substituted alkyl or substituted cycloalkyl wherein the alkyl or cycloalkyl group is substituted with a substituent selected from the group consisting of alkoxy, alkylthio, optionally substituted phenyl, optionally substituted heterocycle; optionally substituted phenyl; optionally substituted heterocycle; alkyl sulfonyl; optionally substituted benzene sulfonyl; an acyl group; and an inorganic or organic cation;

$R^2$ is selected from the group consisting of: alkyl; alkenyl; cycloalkyl; cycloalkenyl; haloalkenyl; alkynyl; haloalkynyl; substituted alkyl or substituted cycloalkyl wherein the alkyl or cycloalkyl group is substituted with a substituent selected from the group consisting of halogen, alkoxy, alkylthio, optionally substituted phenyl, and optionally substituted heterocycle; optionally substituted phenyl; and optionally substituted heterocycle;

$R^3$ is selected from the group consisting of: alkyl; haloalkyl; alkenyl; cycloalkyl; cycloalkenyl; alkynyl; and optionally substituted phenyl;

$R^4$ is selected from the group consisting of: alkynyl; haloalkyl; haloalkenyl; cycloalkyl; cycloalkenyl; substituted alkyl or substituted cycloalkyl wherein the alkyl or cycloalkyl group is substituted with a substituent selected from the group consisting of alkoxy, alkylthio, oxo, acyl, alkoxycarbonyl, (alkoxyimino)alkyl, ketal, carboxylic acid, optionally substituted phenyl, and optionally substituted heterocycle; and optionally substituted heterocycle;

$R^5$ is selected from the group consisting of: alkyl; alkenyl; alkynyl; haloalkyl; haloalkenyl; cycloalkyl; cycloalkenyl; substituted alkyl or substituted cycloalkyl wherein the alkyl or cycloalkyl group is substituted with a substituent selected from the group consisting of alkoxy, alkylthio, oxo, acyl, alkoxycarbonyl, (alkoxyimino)alkyl, ketal, carboxylic acid, optionally substituted phenyl, and optionally substituted heterocycle; and optionally substituted hererocycle;

$R^4$ and $R^5$ together with the carbon to which they are attached form a substituted or unsubstituted saturated or partially saturated heterocyclic or carbocyclic ring containing 3 or more ring atoms. The ring may be bridged or fused and the ring substituents are selected from the group consisting of hydrogen; alkyl; alkenyl; alkynyl; substituted alkyl wherein the alkyl group is substituted with a substituent selected from the group consisting of alkoxy, alkylthio, optionally substituted phenyl, and optionally substituted heterocycle; optionally substituted phenyl; and optionally substituted heterocycle; oxo; acyl; alkoxy; alkylthio; alkoxycarbonyl; (alkoxyimino)alkyl; ketal; and carboxylic acid.

Compounds of Formula (2) within the general scope of the invention include:

6-cyclopropyl-3-[1-(ethoxyimino)butyl]-4-hydroxy-6-methyl-5,6-dihydro-2H-pyran-2-one;

3-[1-(ethoxyimino)butyl]-4-hydroxy-6-methyl-6-(2-thienyl)-5,6-dihydro-2H-pyran-2-one;

3-[1-(ethoxyimino)butyl]-4-hydroxy-7-methyl-1-oxaspiro[5.5]undec-3-en-2-one;

3-[1-ethoxyimino)butyl]-4-hydroxy-8-methyl-1-oxaspiro[5.5]undec-3-en-2-one;

8,10-dimethyl-3-[1-(ethoxyimino)butyl]-4-hydroxy-1-oxaspiro[5.5]undec-3-en-2-one;

3-[1-(ethoxyimino)butyl)-9-ethyl-4-hydroxy-1-oxaspiro[5.5]undec-3-en-2-one;

9-tert-butyl-3-[1-(ethoxyimino)butyl)-4-hydroxy-1-oxaspiro[5.5]undec-3-en-2-one;

3-[1-(ethoxyimino)butyl)-4-hydroxy-1-oxaspiro[5.7]tridec-3-en-2-one; 3-[1-(ethoxyimino)butyl)-4-hydroxy-1-oxaspiro[5.9]pentadec-3-en-2-one;

3-[1-(ethoxyimino)butyl)-4-hydroxy-1-oxaspiro[5.11-]heptadec-3-en-2-one;

5-[1-(allyloxyimino)butyl)-4'-hydroxyspiro[norbornane-2,2'(3'H)-6'H-pyran-6'-one];

5-[1-(ethoxyimino)butyl)-4'-hydroxyspiro[norbornane-2,2'(3H)-6'H-pyran-6'-one];

5-[1-(ethoxyimino)propyl)-4'-hydroxyspiro[norbornane-2,2'(3'H)-6'H-pyran-6'-one];

5-[1-(ethoxyimino)butyl)-4-hydroxyspiro[6H-pyran-6-one-2,(3H), 1'-(1',2',3',4'-tetrahydronaphthalene)];

5-[1-(allyloxyimino)butyl)-4'-hydroxyspiro[perhydronaphthalene-1,2'(3'H)-6'H-pyran-6'-one];

5-[1-(ethoxyimino)butyl)-4'-hydroxyspiro[perhydronaphthalene-1,2'(3'H)-6'H-pyran-6'-one]; and 5-[1-(ethoxyimino)propyl]-4'-hydroxyspiro[perhydronaphthalene-1,2'(3'H)-6'H-pyran-6'-one].

A preferred group of compounds of general Formula (2) consists of spirocyclic derivatives of the general Formulae (3), (4), (5) and (6). For these novel derivatives, $R^1$, $R^2$ and $R^3$ are as specified above. For the spirocyclic derivatives (3), (4) and (5), the non-lactone ring may be saturated or partially unsaturated and $R^6$, $R^7$, $R^8$ and $R^9$ are selected from the group consisting of: hydrogen; halo; alkyl; alkenyl; alkynyl; substituted alkyl wherein the alkyl group is substituted with a substituent selected from the group consisting of halo, alkoxy, alkylthio, optionally substituted phenyl, and optionally substituted heterocycle; optionally substituted phenyl; and optionally substituted heterocycle; oxo; acyl; alkoxy; alkylthio; alkoxycarbonyl; alkoxyimino)alkyl; ketal; and carboxylic acid.

(3)

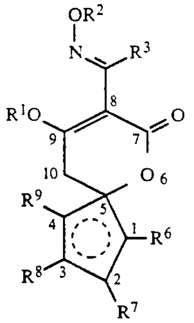

(4)

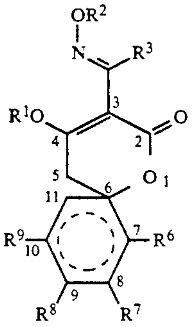

-continued (5)

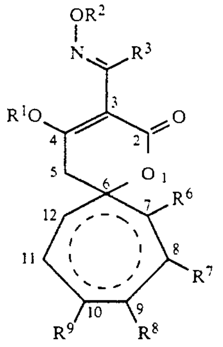

(6)

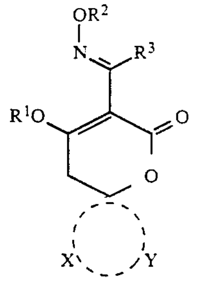

For the novel derivatives (6), the polyatomic ring containing X and Y is a substituted or unsubstituted saturated or partially saturated heterocyclic ring containing 5,6 or 7 ring atoms. The heterocyclic ring may contain one or more heteroatoms selected from the group consisting of oxygen, nitrogen and sulfur, and the ring substituents are selected from the group consisting of: hydrogen; alkyl; alkenyl; oxo; acyl; alkoxy; alkylthio; ketal; alkoxycarbonyl; (alkoxyimino)alkyl; carboxylic acid; substituted alkyl wherein the alkyl group is substituted with a substituent selected from the group consisting of alkoxy, alkythio, optionally substituted phenyl, and optionally substituted heterocycle; optionally substituted phenyl; and optionally substituted heterocycle.

In all of the above alkyl, alkenyl and alkynyl include straight-chain and branched-chain structures.

In all of the above heterocycle means a mono- or polycyclic heterocyclic ring structure that contains one or more heteroatoms and may or may not be aromatic. Suitable heteroatoms are nitrogen, oxygen, and sulphur. The heterocyclic ring preferably has more than three atoms in the ring. Some examples of suitable heterocycle groups are thiophenyl, benzofuranyl, furanyl, morpholino, and pyridyl.

Preferably in all of the above alkyl, alkenyl, and alkynyl mean lower alkyl, alkenyl and alkynyl. More preferably alkyl, alkoxy, alkylthio, haloalkyl, alkyl sulphonyl or substituted alkyl groups contain 1 to 6 carbon atoms and alkenyl, alkynyl, haloalkenyl, or haloalkynyl groups contain 2 to 6 carbon atoms.

It should be recognized that when $R^1$ is hydrogen the compounds (2) of the invention may undergo tautomerism and exist in any one of five forms as shown below.

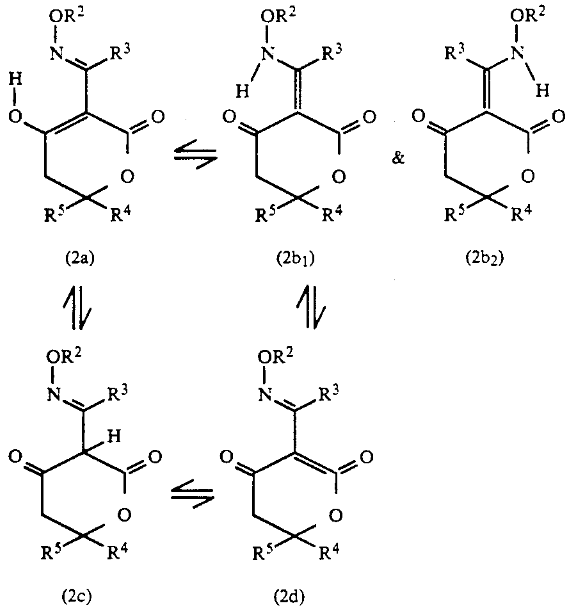

(2a) (2b1) (2b2) (2c) (2d)

All tautomeric forms are included in the scope of this invention.

Particularly preferred choices for $R^1$ include hydrogen and the alkali metal cations.

Preferred choices for $R^2$ include alkyl, alkenyl and haloalkenyl.

Particularly preferred choices for $R^2$ include ethyl, allyl and 2- and 3-chloroallyl.

Particularly preferred choices for $R^3$ include ethyl and n-propyl.

Particularly preferred choices for $R^6$, $R^7$, $R^8$, $R^9$ and substituents on the polyatomic chain XY include H and methyl. Where isomers may exist useful compositions may consist of the isomers separately or in mixtures in any possible ratio.

Specific examples of compounds of the invention of Formula (2) include those compounds detailed in Tables 1-4 below. Table 1 details some examples of compounds of Formula (3) of the invention wherein the cyclopentyl ring is saturated and $R^1=R^6=R^8=R^9=H$; Table 2 details some examples of compounds of Formula (4) of the invention wherein $R^1=R^6=R^7=R^9=H$; Table 3 details some examples of compounds of Formula (5) of the invention wherein $R^1=R^6=R^7=R^8=R^9=H$; and Table 4 details some examples of compounds of Formula (6) of the invention wherein the heterocyclic ring is saturated and X and/or Y are sulfur and wherein $R^1$ and the heterocyclic ring substituents are hydrogen.

TABLE 1

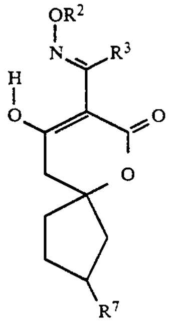

(3)

| Compound | $R^2$ | $R^3$ | $R^7$ |
|---|---|---|---|
| 3.1 | ethyl | n-propyl | H |
| 3.2 | $CH_2-CH=CH_2$ | n-propyl | H |
| 3.3 | $CH_2-CCl=CH_2$ | n-propyl | H |
| 3.4 | $CH_2-CH=CHCl$ | n-propyl | H |
| 3.5 | ethyl | ethyl | H |
| 3.6 | $CH_2-CH=CH_2$ | ethyl | H |
| 3.7 | $CH_2-CCl=CH_2$ | ethyl | H |
| 3.8 | $CH_2-CH=CHCl$ | ethyl | H |
| 3.9 | ethyl | n-propyl | methyl |
| 3.10 | $CH_2-CH=CH_2$ | n-propyl | methyl |
| 3.11 | $CH_2-CCl=CH_2$ | n-propyl | methyl |
| 3.12 | $CH_2-CH=CHCl$ | n-propyl | methyl |
| 3.13 | ethyl | ethyl | methyl |
| 3.14 | $CH_2-CH=CH_2$ | ethyl | methyl |
| 3.15 | $CH_2-CCl=CH_2$ | ethyl | methyl |
| 3.16 | $CH_2-CH=CHCl$ | ethyl | methyl |

TABLE 2

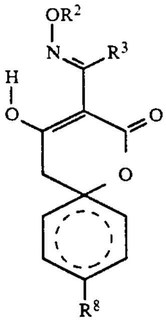

(4)

| Compound | $R^2$ | $R^3$ | $R^8$ | 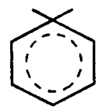 |
|---|---|---|---|---|
| 4.1 | ethyl | n-propyl | H | cyclohexylidene |
| 4.2 | $CH_2-CH=CH_2$ | n-propyl | H | cyclohexylidene |
| 4.3 | $CH_2-CCl=CH_2$ | n-propyl | H | cyclohexylidene |
| 4.4 | $CH_2-CH=CHCl$ | n-propyl | H | cyclohexylidene |
| 4.5 | ethyl | ethyl | H | cyclohexylidene |
| 4.6 | $CH_2-CH=CH_2$ | ethyl | H | cyclohexylidene |
| 4.7 | $CH_2-CCl=CH_2$ | ethyl | H | cyclohexylidene |

TABLE 2-continued

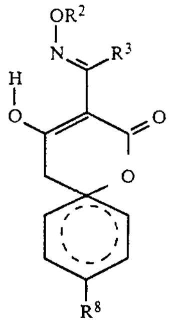

(4)

| Compound | $R^2$ | $R^3$ | $R^8$ | 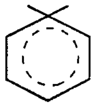 |
|---|---|---|---|---|
| 4.8 | $CH_2—CH═CHCl$ | ethyl | H | cyclohexylidene |
| 4.9 | ethyl | n-propyl | $CH_3$ | cyclohexylidene |
| 4.10 | $CH_2—CH═CH_2$ | n-propyl | $CH_3$ | cyclohexylidene |
| 4.11 | $CH_2—CCl═CH_2$ | n-propyl | $CH_3$ | cyclohexylidene |
| 4.12 | $CH_2—CH═CHCl$ | n-propyl | $CH_3$ | cyclohexylidene |
| 4.13 | $CH_2—C≡CH$ | n-propyl | $CH_3$ | cyclohexylidene |
| 4.14 | $CH(CH_3)CO_2CH_2CH_3$ | n-propyl | $CH_3$ | cyclohexylidene |
| 4.15 | ethyl | ethyl | $CH_3$ | cyclohexylidene |
| 4.16 | $CH_2—CH═CH_2$ | ethyl | $CH_3$ | cyclohexylidene |
| 4.17 | $CH_2—CCl═CH_2$ | ethyl | $CH_3$ | cyclohexylidene |
| 4.18 | $CH_2—CH═CHCl$ | ethyl | $CH_3$ | cyclohexylidene |
| 4.19 | ethyl | n-propyl | H | 2-cyclohexen-1-ylidene |
| 4.20 | $CH_2—CH═CH_2$ | n-propyl | H | 2-cyclohexen-1-ylidene |
| 4.21 | $CH_2—CCl═CH_2$ | n-propyl | H | 2-cyclohexen-1-ylidene |
| 4.22 | $CH_2—CH═CHCl$ | n-propyl | H | 2-cyclohexen-1-ylidene |
| 4.23 | ethyl | n-propyl | H | 2-cyclohexen-1-ylidene |
| 4.24 | $CH_2—CH═CH_2$ | n-propyl | H | 2-cyclohexen-1-ylidene |
| 4.25 | $CH_2—CCl═CH_2$ | n-propyl | H | 2-cyclohexen-1-ylidene |
| 4.26 | $CH_2—CH═CHCl$ | n-propyl | H | 2-cyclohexen-1-ylidene |

TABLE 3

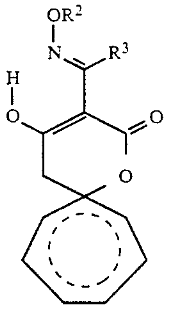

(5)

| Compound | $R^2$ | $R^3$ | 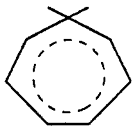 |
|---|---|---|---|
| 5.1 | ethyl | n-propyl | cycloheptylidene |
| 5.2 | $CH_2—CH═CH_2$ | n-propyl | cycloheptylidene |
| 5.3 | $CH_2—CCl═CH_2$ | n-propyl | cycloheptylidene |
| 5.4 | $CH_2—CH═CHCl$ | n-propyl | cycloheptylidene |
| 5.5 | $CH_2—C≡CH$ | n-propyl | cycloheptylidene |
| 5.6 | ethyl | ethyl | cycloheptylidene |
| 5.7 | $CH_2—CH═CH_2$ | ethyl | cycloheptylidene |
| 5.8 | $CH_2—CCl═CH_2$ | ethyl | cycloheptylidene |
| 5.9 | $CH_2—CH═CHCl$ | ethyl | cycloheptylidene |

TABLE 3-continued

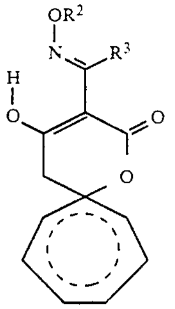

(5)

| Compound | $R^2$ | $R^3$ | 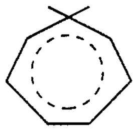 |
|---|---|---|---|
| 5.10 | ethyl | n-propyl | 2-cyclohepten-1-ylidene |
| 5.11 | $CH_2—CH═CH_2$ | n-propyl | 2-cyclohepten-1-ylidene |
| 5.12 | $CH_2—CCl═CH_2$ | n-propyl | 2-cyclohepten-1-ylidene |
| 5.13 | $CH_2—CH═CHCl$ | n-propyl | 2-cyclohepten-1-ylidene |
| 5.14 | ethyl | ethyl | 2-cyclohepten-1-ylidene |
| 5.15 | $CH_2—CH═CH_2$ | ethyl | 2-cyclohepten-1-ylidene |
| 5.16 | $CH_2—CCl═CH_2$ | ethyl | 2-cyclohepten-1-ylidene |
| 5.17 | $CH_2—CH═CHCl$ | ethyl | 2-cyclohepten-1-ylidene |

TABLE 4

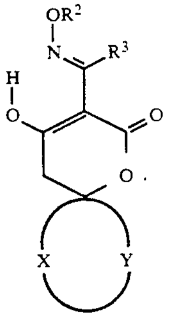

(6)

| Compound | $R^2$ | $R^3$ | 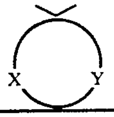 |
|---|---|---|---|
| 6.1 | ethyl | n-propyl | tetrahydrothiophen-3-ylidene |
| 6.2 | $CH_2-CH=CH_2$ | n-propyl | tetrahydrothiophen-3-ylidene |
| 6.3 | $CH_2-CCl=CH_2$ | n-propyl | tetrahydrothiophen-3-ylidene |
| 6.4 | $CH_2-CH=CHCl$ | n-propyl | tetrahydrothiophen-3-ylidene |
| 6.5 | ethyl | ethyl | tetrahydrothiophen-3-ylidene |
| 6.6 | $CH_2-CH=CH_2$ | ethyl | tetrahydrothiophen-3-ylidene |
| 6.7 | $CH_2-CCl=CH_2$ | ethyl | tetrahydrothiophen-3-ylidene |
| 6.8 | $CH_2-CH=CHCl$ | ethyl | tetrahydrothiophen-3-ylidene |
| 6.9 | ethyl | n-propyl | tetrahydrothiophen-3-ylidene |
| 6.10 | $CH_2-CH=CH_2$ | n-propyl | tetrahydrothiophen-3-ylidene |
| 6.11 | $CH_2-CCl=CH_2$ | n-propyl | tetrahydrothiophen-3-ylidene |
| 6.12 | $CH_2-CH=CHCl$ | n-propyl | tetrahydrothiophen-3-ylidene |
| 6.13 | ethyl | ethyl | tetrahydrothiopyran-3-ylidene |
| 6.14 | $CH_2-CH=CH_2$ | ethyl | tetrahydrothiopyran-3-ylidene |
| 6.15 | $CH_2-CCl=CH_2$ | ethyl | tetrahydrothiopyran-3-ylidene |
| 6.16 | $CH_2-CH=CHCl$ | ethyl | tetrahydrothiopyran-3-ylidene |
| 6.17 | ethyl | n-propyl | tetrahydrothiopyran-4-ylidene |
| 6.18 | $CH_2-CH=CH_2$ | n-propyl | tetrahydrothiopyran-4-ylidene |
| 6.19 | $CH_2-CCl=CH_2$ | n-propyl | tetrahydrothiopyran-4-ylidene |
| 6.20 | $CH_2-CH=CHCl$ | n-propyl | tetrahydrothiopyran-4-ylidene |
| 6.21 | ethyl | ethyl | tetrahydrothiopyran-4-ylidene |
| 6.22 | $CH_2-CH=CH_2$ | ethyl | tetrahydrothiopyran-4-ylidene |
| 6.23 | $CH_2-CCl=CH_2$ | ethyl | tetrahydrothiopyran-4-ylidene |
| 6.24 | $CH_2-CH=CHCl$ | ethyl | tetrahydrothiopyran-4-ylidene |
| 6.25 | ethyl | n-propyl | 1,4-dithiacyclohept-6-ylidene |
| 6.26 | $CH_2-CH=CH_2$ | n-propyl | 1,4-dithiacyclohept-6-ylidene |
| 6.27 | $CH_2-Cl=CH_2$ | n-propyl | 1,4-dithiacyclohept-6-ylidene |
| 6.28 | $CH_2-CH=CHCl$ | n-propyl | 1,4-dithiacyclohept-6-ylidene |
| 6.29 | ethyl | ethyl | 1,4-dithiacyclohept-6-ylidene |
| 6.30 | $CH_2-CH=CH_2$ | ethyl | 1,4-dithiacyclohept-6-ylidene |
| 6.31 | $CH_2-CCl=CH_2$ | ethyl | 1,4-dithiacyclohept-6-ylidene |
| 6.32 | $CH_2-CH=CHCl$ | ethyl | 1,4-dithiacyclohept-6-ylidene |

The compounds of the invention may be prepared from the dianion of an acetoacetate ester by condensation with an appropriate ketone (cf. Huckin, S. N., and Weiler, L., *Can. J. Chem.*, 1974, 52, 2157) followed by cyclization with or without intermediate hydrolysis to novel tetrahydro-2H-pyran-2,4-diones (Formula 7) (Reaction Scheme 1 below). The pyrandiones or their tautomeric 4-hydroxy-5,6-dihydro-2H-pyran-2-ones can also be obtained by customary methods described in the literature. The 6,6-disubstituted pyran-2,4-diones thus obtained may be acylated on oxygen and the enol esters isomerized (Fries rearrangement) to give novel C-substituted products (Formula 8). The C-acylated derivatives may be reacted with O-substituted hydroxylamines to afford derivatives of the general Formula (2) wherein $R^1$ is hydrogen.

Reaction Scheme 1

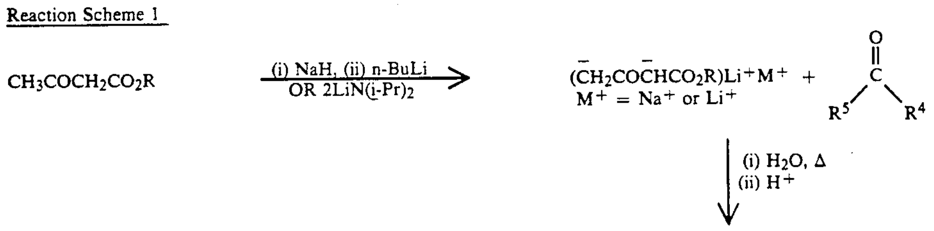

-continued

Reaction Scheme 1

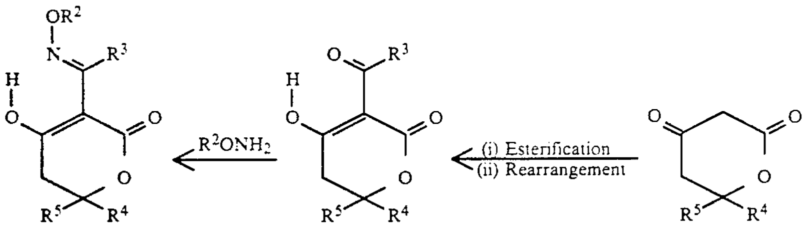

(2; $R^1$ = H) (8) (7)

Compounds of the invention of Formula (2) wherein $R^1$ is not hydrogen may be prepared by standard synthetic procedures. For example, compounds of the invention of Formula (2) wherein $R^1$ is an inorganic or organic cation may be prepared from compounds of the invention of Formula (2) wherein $R^1$ is hydrogen by reacting these latter compounds with an appropriate inorganic or organic base. Esterification of the vinylogous acid in compounds of Formula (2) wherein $R^1$ is hydrogen provides further herbicidal and growth regulating derivatives.

Compounds of Formula (7) and (8) where $R^3$, $R^4$ and $R^5$ are as hereinbefore defined are novel. The scope of the invention includes these compounds. Specific examples of compounds of the invention of Formula (7) include those compounds detailed in Table 5 below.

TABLE 5

(7)

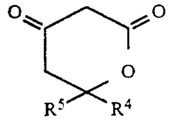

6,6-Disubstituted-5,6-dihydro-2H-pyran-2,4-diones

| Compound | |
|---|---|
| | 6,6-Geminal substituents |
| 7.2 | cyclopropyl, methyl |
| 7.4 | methyl, 2-thienyl |
| | Spirocyclic compounds |
| 7.5 | 6-oxaspiro[4.5]deca-7,9-dione |
| 7.6 | 2-methyl-6-oxaspiro[4.5]deca-7,9-dione |
| 7.7 | 1-oxaspiro[5.5]undeca-2,4-dione |
| 7.8 | 7 methyl-1-oxaspiro[5.5]undeca-2,4-dione |
| 7.9 | 8-methyl-1-oxaspiro[5.5]undeca-2,4-dione |
| 7.10 | 9-methyl-1-oxaspiro[5.5]undeca-2,4-dione |
| 7.11 | 8,10-dimethyl-1-oxaspiro[5.5]deca-7,9-dione |
| 7.12 | 9-ethyl-1-oxaspiro[5.5]undeca-2,4-dione |
| 7.13 | 9-tert-butyl-1-oxaspiro[5.5]undeca-2,4-dione |
| 7.14 | 1-oxaspiro[5.5]undec-7-en-2,4-dione |
| 7.15 | 1-oxaspiro[5.6]dodeca-2,4-dione |
| 7.16 | 1-oxaspiro[5.6]dodec-7-en-2,4-dione |
| 7.17 | 1-oxaspiro[5.7]trideca-2,4-dione |
| 7.18 | 1-oxaspiro[5.9]pentadeca-2,4-dione |
| 7.19 | 1-oxaspiro[5.11]heptadeca-2,4-dione |
| 7.20 | spiro[norbornane-2,2'-tetrahydro-6'H-pyran-4',6'-dione] |
| 7.21 | spiro[tetrahydro-6 H-pyran-4,6-dione-2(3H),1'-(1',2',3',4'-tetrahydronaphthalene)] |
| 7.22 | spiro[perhydronaphthalene-1,2' tetrahydro-6'H- |

TABLE 5-continued (7)

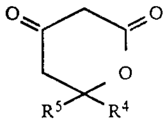

6,6-Disubstituted-5,6-dihydro-2H-pyran-2,4-diones

| Compound | |
|---|---|
| | pyran-4',6'-dione] |
| 7.23 | 6-oxa-2-thiaspiro[4.5]deca-7,9-dione |
| 7.24 | 1-oxa-8-thiaspiro[5.5]undeca-2,4-dione |
| 7.25 | 1-oxa-9-thiaspiro[5.5]undeca-2,4-dione |
| 7.26 | 1-oxa-8,11-dithiaspiro[5.6]dodeca-2,4-dione |

It should be recognized that tautomerization is possible for the compounds (7) of the invention and that they may exist in any one of three tautomeric forms as shown below.

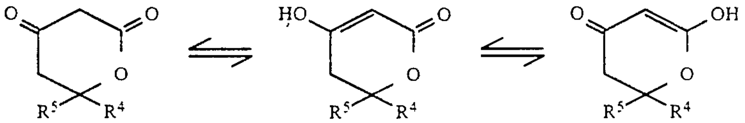

(7a) (7b) (7c)

All tautomeric and isomeric forms of compounds of Formula (7) are included in the scope of this invention.

Specific examples of compounds of the invention of Formula (8) include those compounds detailed in Table 6.

TABLE 6

(8)

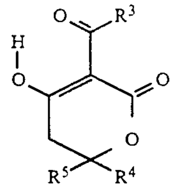

3-Acyl-4-hydroxy-6,6-disubstituted-5,6-dihydro-2H-pyran-2-ones

| Compound | | |
|---|---|---|
| | 6,6-Geminal substituents | $R^3$ |
| 8.3 | cyclopropyl, methyl | n-propyl |
| 8.4 | cyclopropyl, methyl | ethyl |
| 8.7 | methyl, 2-thienyl | n-propyl |
| 8.8 | methyl, 2-thienyl | ethyl |
| | Spirocyclic compounds | |
| 8.9 | 9-hydroxy-8-propionyl-6-oxaspiro[4.5]dec-8-en-7-one | |
| 8.10 | 8-butyryl-9-hydroxy-6-oxaspiro[4.5]dec-8-en-7-one | |
| 8.11 | 9-hydroxy-2-methyl-8-propionyl-6-oxaspiro[4.5]dec-8-en-7-one | |

TABLE 6-continued

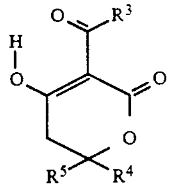

(8)

3-Acyl-4-hydroxy-6,6-disubstituted-5,6-dihydro-2H-pyran-2-ones

| Compound | |
|---|---|
| 8.12 | 8-butyryl-9-hydroxy-2-methyl-6-oxaspiro[4.5]dec-8-en-7-one |
| 8.13 | 4-hydroxy-3-propionyl-1-oxaspiro[5.5]undec-3-en-2-one |
| 8.14 | 3-butyryl-4-hydroxy-1-oxaspiro[5.5]undec-3-en-2-one |
| 8.15 | 4-hydroxy-7-methyl-3-propionyl-1-oxaspiro[5.5]undec-3-en-2-one |
| 8.16 | 3-butyryl-4-hydroxy-7-methyl-1-oxaspiro[5.5]undec-3-en-2-one |
| 8.17 | 4-hydroxy-8-methyl-3-propionyl-1-oxaspiro[5.5]undec-3-en-2-one |
| 8.18 | 3-butyryl-4-hydroxy-8-methyl-1-oxaspiro[5.5]undec-3-en-2-one |
| 8.19 | 4-hydroxy-9-methyl-3-propionyl-1-oxaspiro[5.5]undec-3-en-2-one |
| 8.20 | 3-butyryl-4-hydroxy-9-methyl-1-oxaspiro[5.5]undec-3-en-2-one |
| 8.21 | 8,10-dimethyl-4-hydroxy-3-propionyl-1-oxaspiro[5.5]undec-3-en-2-one |
| 8.22 | 8,10-dimethyl-3-butyryl-4-hydroxy-1-oxaspiro[5.5]undec-3-en-2-one |
| 8.23 | 9-ethyl-4-hydroxy-3-propionyl-1-oxaspiro[5.5]undec-3-en-2-one |
| 8.24 | 3-butyryl-9-ethyl-4-hydroxy-1-oxaspiro[5.5]undec-3-en-2-one |
| 8.25 | 9-tert-butyryl-4-hydroxy-3-propionyl-1-oxaspiro[5.5]undec-3-en-2-one |
| 8.26 | 9-tert-3-butyryl-4-hydroxy-1-oxaspiro[5.5]undec-3-en-2-one |
| 8.27 | 4-hydroxy-3-propionyl-1-oxaspiro[5.5]undeca-3,7-dien-2-one |
| 8.28 | 3-butyryl-4-hydroxy-1-oxaspiro[5.5]undeca-3,7-dien-2-one |
| 8.29 | 4-hydroxy-3-propionyl-1-oxaspiro[5.6]dodec-3-en-2-one |
| 8.30 | 3-butyryl-4-hydroxy-1-oxaspiro[5.6]dodec-3-en-2-one |
| 8.31 | 4-hydroxy-3-propionyl-1-oxaspiro[5.6]dodeca-3,7-dien-2-one |
| 8.32 | 3-butyryl-4-hydroxy-1-oxaspiro[5.6]dodeca-3,7-dien-2-one |
| 8.33 | 4-hydroxy-3-propionyl-1-oxaspiro[5.6]tridec-3-en-2-one |
| 8.34 | 3-butyryl-4-hydroxy-1-oxaspiro[5.6]tridec-3-en-2-one |
| 8.35 | 4-hydroxy-3-propionyl-1-oxaspiro[5.6]pentadec-3-en-2-one |
| 8.36 | 3-butyryl-4-hydroxy-1-oxaspiro[5.6]pentadec-3-en-2-one |
| 8.37 | 4-hydroxy-3-propionyl-1-oxaspiro[5.6]heptadec-3-en-2-one |
| 8.38 | 3-butyryl-4-hydroxy-1-oxaspiro[5.6]heptadec-3-en-2-one |
| 8.39 | 4'-hydroxy-5'-propionylspiro[norbornane-2,2'(3'H)-6'H-pyran-6'one] |
| 8.40 | 5'-butyryl-4-hydroxyspiro[norbornane-2,2(3'H)-6'H-pyran-6'one] |
| 8.41 | 4-hydroxy-5-propionylspiro[6H-pyran-6-one-2(3H),1'-(1',2',3',4'-tetrahydronaphthalene)] |
| 8.42 | 5-butyryl-4-hydroxyspiro[6H-pyran-6-one-2(3H), 1'-(1',2',3',4'-tetrahydronaphthalene)] |
| 8.43 | 4'-Hydroxy-5'-propionylspiro[perhydronaphthalene-1,2'(3'H)-6'-H-pyran-6'-one] |
| 8.44 | 5'-butyryl-4'-hydroxyspiro[perhydronaphthalene-1,2'(3'H)-6'H-pyran-6'-one] |
| 8.45 | 9-hydroxy-8-propionyl-6-oxa-2-thiaspiro[4.5]dec-8-en-7-one |
| 8.46 | 8-butyryl-9-hydroxy-6-oxa-2-thiaspiro[4.5]dec-8-en-7-one |
| 8.47 | 4-hydroxy-3-propionyl-1-oxa-8-thiaspiro[5.5]undec-3-en-2-one |
| 8.48 | 3-butyryl-4-hydroxy-1-oxa-8-thiaspiro[5.5]undec-3-en-2-one |
| 8.49 | 4-hydroxy-3-propionyl-1-oxa-9-thiaspiro[5.5]undec-3-en-2-one |
| 8.50 | 3-butyryl-4-hydroxy-1-oxa-9-thiaspiro[5.5]undec-3-en-2-one |
| 8.51 | 4-hydroxy-3-propionyl-1-oxa-8,11-dithiaspiro[5.6]dodec-3-en-2-one |
| 8.52 | 3-butyryl-4-hydroxy-1-oxa-8,11-dithiaspiro[5.6]dodec-3-en-2-one |

TABLE 6-continued

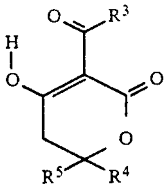

(8)

3-Acyl-4-hydroxy-6,6-disubstituted-5,6-dihydro-2H-pyran-2-ones

It should be recognized that the compounds (8) of the invention may undergo tautomerism and exist in any one of five forms as shown below.

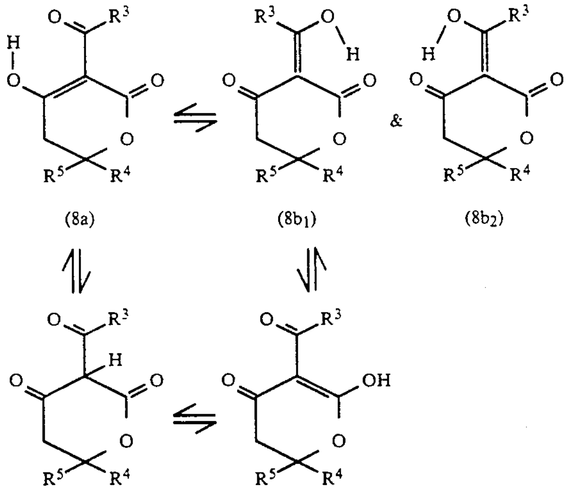

(8a) (8b1) & (8b2)

(8c) (8d)

All tautomeric and isomeric forms of compounds of Formula (8) are included in the scope of this invention.

The compounds of Formula (2) may be applied directly to the plant (post-emergence application) or to the soil before the emergence of the plant (pre-emergence application).

The compounds of the invention are substantially more effective against monocotyledenous plants or grass species than against dicotyledenous plants or broad-leaved species.

In either pre-emergent (soil treatment) or post emergent (foliar) application the compounds of the invention are superior to the prior art compounds in their selectivity for weed grasses in broad-leafed crops. As demonstrated by the examples given at the end of this description, application of the quantity of compound necessary to kill weed grasses such as *Setaria anceps* or *Echinochloa crus-galli* does not harm broad-leaf crops such as soy bean, sugar beet, rape, tomator or squash.

Certain of the compounds of Formula (2) show selective herbicidal activity against wild grasses in monocotyledenous crop species and hence may be used for selective control of wild grass in graminaceous crops.

The compounds of Formula (2) may be used on their own to inhibit the growth of, severely damage, or kill plants but are preferably used in the form of a composition comprising a compound of the invention in admixture with an inert carrier comprising a solid or liquid diluent.

Therefore, in yet a further aspect the invention provides plant growth inhibiting, plant damaging, or plant killing compositions comprising a compound of Formula (2) as hereinbefore defined and an inert carrier therefor.

The compositions of the invention may comprise, in addition to one or more compounds of the invention, one or more compounds not of the invention but which possess biological activity. For example, as herein before indicated the compounds of the invention are in general substantially more effective against monocotyledonous plants or grass species than against dicotyledonous plants or broad-leaved species. As a result, in certain applications the herbicidal use of the compounds of the invention alone may not be sufficient to protect a crop.

Accordingly in yet a still further embodiment the invention provides a herbicidal composition comprising a mixture of at least one herbicidal compound of Formula (2) as hereinbefore defined with at least one other herbicide.

Certain of the compounds of Formula (2) exhibit useful plant growth regulating activity. For example, while certain compounds of Formula (2) show selective herbicidal activity against wild grasses in crops of cultivated plants, at some rates of application they exhibit plant growth regulating effects in said crops. Certain of the compounds of Formula (2) may be used for selective control of wild grass in graminaceous crops.

Plant growth regulating effects may be manifested in a number of ways. For example, suppression of apical dominance, stimulation auxiliary bud growth, stimulation of early flowering and seed formation, enhancement of flowering and increase in seed yield, stem thickening, stem shortening and tillering. Plant growth regulating effects shown by compounds of the invention include, for example, tillering and stem shortening in crops such as wheat and barley.

Accordingly in a still further aspect the invention provides a process for regulating the growth of a plant which process comprises applying to the plant, to the seed of the plant, or to the growth medium of the plant, an effective amount of a compound Formula (2), as hereinbefore defined.

To effect the plant growth regulating process of the present invention the compounds of Formula (2) may be applied directly to the plant (post-emergence application) or to the seed or soil before the emergence of the plant (pre-emergence) application.

The compounds of Formula (2) may be used on their own to regulate the growth of plants but in general are preferably used in the form of a composition comprising a compound of the invention in admixture with a carrier comprising a solid or liquid diluent.

Therefore, in a still further aspect the invention provides plant growth regulating compositions comprising a compound of Formula (2) as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the type of formulation and whether the composition is ready for use such as, for example, a dust formulation or an aqueous emulsion or whether the composition is a concentrate such as, for example, an emulsifiable concentrate or a wettable powder, which is suitable for dilution before use. The present invention includes both types of composition, accordingly the compositions to the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, talc, chalk, dolomite, limestone, lime, calcium carbonate, powdered magnesia, magnesium oxide, magnesium sulfate, gypsum, calcium sulfate, pyrophyllite, silicic acid, silicates and silica gels; fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acid, the di- and triisopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with fatty alcohols such as oleyl alcohol and cetyl alcohol; the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oxide/propylene oxide block copolymers; lauryl alcohol polyglycol ether acetal; and the lecithins.

The liquid compositions may comprise a solution or dispersion of the active ingredient in a liquid carrier optionally containing one or more surface active agents which act as wetting, emulsifying and/or dispersing agents. Examples of liquid carriers include: water; mineral oil fractions such as, for example, kerosene, solvent naphtha, petroleum, coal tar oils and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, cyclohexanone and isophorone; and strongly polar organic solvents such as, for example, N,N-dimethylformamide, dimethyl sulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 20 to 99%, preferably 20 to 60%, by weight of active ingredient.

Emulsions or emulsifiable concentrates of the salts are conveniently prepared by dissolving the active ingredient in an organic solvent containing one or more surface active agents used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.005 to 20 kilograms per hectare is suitable while from 0.01 to 5.0 kilograms per hectare may be preferred.

The invention is now illustrated by but in no way limited to the following examples. These examples of compounds of the invention were made by the same general procedure, starting from the dianion of acetoacetate and an appropriate ketone: the dianion of the acetoacetate was made by one of two ways.

General Procedure for Preparation of Examples of Compounds of the Invention

(a) Synthesis of the Pyran-2,4-diones (7)

To a stirred solution of the sodium salt of methyl acetoacetate [ca. 55 mmol, either preformed (7.60 g) or made in situ from methyl acetoacetate (5.93 ml, 55 mmol) and sodium hydride (55 mmol) according to the method of Huckin, S. N., and Weiler, L., *Can. J. Chem.*, 1974, 52, 2157] in dry tetrahydrofuran (50 ml) under nitrogen and cooled to 0° C., was added dropwise a solution of n-butyllithium (21.2 ml, 2.6M in hexane, 55 mmol). After 1 h the mixture was treated with an appropriate ketone (50 mmol) (solid ketones were dissolved in tetrahydrofuran prior to addition) and left stirring at 0° C. for 120 min before being quenched with methanol (2.4 ml, 60 mmol). After addition of further methanol (20 ml) and water (10 ml) [and in certain instances acid; e.g., in Example 10, acetic acid (3.2 ml, 56 mmol) was added] the mixture was boiled for ca. 30 min then diluted further with water (40 ml) and concentrated (to ca. 40 ml) at reduced pressure. Upon cooling and addition of water (ca. 150 ml) the mixture was extracted with ether ($2\times100$ ml). The ether extracts were washed with water (50 ml); and the combined aqueous phases were acidified to pH 1–2 with conc. hydrochloric acid and extracted with ether (100 ml). (At this stage of some reactions a first crop of the pyrandione crystallized from the ether solution and was recovered by filtration.) The ether solution was then evaporated and the residual water removed from the product mixture by azeotropic distillation with ethanol/benzene and then with benzene. The residue was either chromatographed ($SiO_2$, dichloromethane) or, in some instances, crystallization of the pyrandione was achieved by diluting a concentrated benzene solution (ca. 20 ml) of the residue cautiously with cyclohexane to a faint turbidity, and then stirring vigorously. When crystallization ensured, the mixture was cautiously diluted with more cyclohexane (ca. 20 ml) and stirred for a further 4 h, after which the precipitate was collected and washed with cyclohexane/benzene (4:1) to afford the pyrandione (7).

Method B

A solution of n-butyllithium (45 ml, 2.45M in hexane, 110 mmol) was added to a stirred solution of diisopropylamine (15.6 ml, 111 mmol) in tetrahydrofuran (50 ml) maintained at 0° C. under argon. The stirring was continued for 15 min at room temperature; the mixture was then chilled in ice. Methyl acetoacetate (5.67 ml, 52.5 mmol) was then added and the resultant mixture stirred at 0° C. for 30 min; whereupon an appropriate ketone (50 mmol dissolved in the minimum quantity of tetrahydrofuran to form a homogeneous solution) was added and stirring continued for an additional 90 min (or until the reaction mixture paled to light orange or yellow) before quenching with methanol (4.8 ml, 120 mmol). The reaction mixture was then worked up as in Method A to give the pyrandione (7).

(b) Acylation of Pyrandiones

To a stirred solution of the pyrandione (7) (6.10 mmol) and DBU [1,8-diazabicyclo(5.4.0.)-7-undecene] (0.99 g, 6.5 mmol) in toluene (20 ml) at 0° C. was added an appropriate acyl chloride (6.6 mmol) and the mixture stirred at 0° C. for 2 h, then at room temperature for 24 h. Dilution with water (50 ml) and toluene (30 ml) and shaking the mixture gave an organic phase which was quickly washed with 5% hydrochloric acid, dried (sodium sulfate) and evaporated in vacuo. The residue and 4-dimethylaminopyridine (40 mg, 0.3 mmol) were heated under reflux in toluene (10 ml) for 3 h (or until thin layer chromatography showed that the reaction was complete) and then the toluene was removed in vacuo and the residue chromatographed [$SiO_2$, dichloromethane:light petroleum (b.p. 40°-60° C.):ethyl acetate (4:4:1)] to give the C-acylated compound (8).

(c) Oximation of Acylated Compounds

A mixture of the C-acylated compound (8) (3.75 mmol), the appropriate O-substituted hydroxylamine hydrochloride (4.00 mmol), triethylamine (0.41 g, 4.0 mmol) and methanol (5 ml) was stirred at room temperature for 48 h, then poured into water (50 ml). Acidification of the mixture to pH 4 with 5M hydrochloric acid, extraction with diethyl ether or ethyl acetate (2×50 ml), evaporation of the organic phase and chromatography [$SiO_2$, dichloromethane or dichloromethane:light petroleum (b.p. 40°-60° C.):ethyl acetate (4:4:1)] of the residue then afforded examples of compounds of the invention (2).

The compounds made using Method A include those in the following examples (1-8).

EXAMPLE 1

Preparation of 3-[1-(Ethoxyimino)butyl]-4-hydroxy-9-methyl-1-oxaspiro[5.5]undec-3-en-2-one (4.9)

(a) 9-Methyl-1-oxaspiro[5.5]undeca-2,4-dione (7.10)

4-Methylcyclohexanone (6.2 ml, 51 mmol) was reacted with the dianion of methyl acetoacetate (ca. 55 mmol) as described in Method A above. The pyrandione (7.10)(6.51 g, 65%) crystallized from benzene/cyclohexane as a white powder m.p. 161°-163° C. Mass spectrum m/z 197 (M+1). $^{13}C$ n.m.r. δ($CDCl_3$) 200.5, C4; 167.4, C2; 81.50, C6; 46.06, C5; 44.53, C3; 36.08; 30.61; 20.85, $CH_3$. $^1H$ n.m.r. δ($CDCl_3$) 3.42, s. 2H3; 2.77, s, 2H5; 1.95-1.4, complex, 7H; 1.2-0.98, m, 2H; 0.93, d, J 6 Hz, $CH_3$.

(b) 3-Butyryl-4-hydroxy-9-methyl-1-oxaspiro[5.5]undec-3-en-2-one (8.20)

The pyrandione (7.10)(1.20 g, 6.11 mmol) was acylated with butyryl chloride (0.70 g, 6.57 mmol) in the presence of DBU, and the O-butyryl intermediate rearranged by heating with 4-dimethylaminopyridine, as described in Part (b) of the general procedure above, to afford the C-acylated compound (8.20)(1.06 g, 65%) as pale yellow granules m.p. 60°-63° C. Mass spectrum m/z 267 (M+1). $^1H$ n.m.r. δ($CDCl_3$) 17.85, broad s, OH; 3.02, t, J 7 Hz, $\underline{CH_2}CH_2CH_3$; 2.85-2.7, m, 2H5; 2.0-1.3, complex, 11H; 0.98, t, J 7.5 Hz, $CH_2CH_2\underline{CH_3}$; 0.94, d, J 6 Hz, $CH_3$. $\nu_{max}$ (nujol) 1723 s, 1690 m, 1644 m, 1567 s, 1462 s, 1068 m $cm^{-1}$.

(c) 3-[1-(Ethoxyimino)butyl]-4-hydroxy-9-methyl-1-oxaspiro[5.5]undec-3-en-2-one (4.9)

The acylated compound (8.20)(1.00 g, 3.75 mmol) was oximated with ethoxyamine hydrochloride (0.39 g, 4.0 mmol) in the presence of triethylamine as described in Part (c) of the general procedure above, to afford the title compound (4.9)(1.00 g, 86%) as a mobile pale yellow oil. (Found: M, 309.196. $C_{17}H_{27}NO_4$ requires 309.194.) $^1H$ n.m.r. δ($CDCl_3$) 14.80, very broad s, 1H; 4.08, q, J 7 Hz, $O\underline{CH_2}CH_3$; 3.00, t, J 7.5 Hz, $\underline{CH_2}CH_2CH_3$; 2.68, s, 2H5; 2.2-1.2 complex, 11H; 1.30, t, J 7.5 Hz, $OCH_2\underline{CH_3}$; 1.15-0.7, m, $CH_2CH_2\underline{CH_3}$ and $CH_3$.

EXAMPLE 2

3-[1-[(2-chloro-2-propenyl)oxyimino]butyl]-4-hydroxy-9-methyl-1-oxaspiro[5.5]undec-3-en-2-one (4.11) [from 4-methylcyclohexanone, butyryl chloride and (2-chloro-2-propenyl)oxyamine hydrochloride] as a viscous light yellow oil which solidified to a white waxy solid m.p. 64°-68° C. Mass spectrum m/z 356 (M+1). $^1H$ n.m.r. δ($CDCl_3$) 5.57, unresolved d, $=CH_2$; 4.65, s, $OCH_2$; 3.00, t, J 7.5 Hz, $\underline{CH_2}CH_2CH_3$; 2.73, s, 2H5; 2.4-0.7 m, 17H.

EXAMPLE 3

3-[1-(Ethoxyimino)butyl]-4-hydroxy-1-oxaspiro[5.5]undeca-3,7-dien-2-one (4.19) (from 2-cyclohexen-1-one, butyryl chloride and ethoxyamine hydrochloride) as a viscous light yellow oil. (Found: M+H, 294.170. $C_{16}H_{23}NO_4$+H requires 294.171.) $^1H$ n.m.r. δ($CDCl_3$) 14.96, very broad s, 1H; 6.10-5.77, m, 2x=CH; 4.11, q, J 7 Hz, $O\underline{CH_2}CH_3$; 3.03, t, J 7.5 Hz, $\underline{CH_2}CH_2CH_3$; 2.68, s, 2H5; 2.45-1.4, m, 8H: 1.37, t, J 7.5 Hz, $OCH_2\underline{CH_3}$; 1.02, t, J 7.5 Hz; $CH_2CH_2\underline{CH_3}$. $\nu_{max}$ (film) 1706 s, 1623 s, 1407 s, 1048 s $cm^{-1}$.

EXAMPLE 4

8-[1-(Ethoxyimino)butyl]-9-hydroxy-6-oxaspiro[4.5]dec-8-en-7-one (3.1) (from cyclopentanone, butyryl chloride and ethoxyamine hydrochloride) as a pale yellow oil. (Found: M, 281.164. $C_{15}H_{23}NO_4$ requires 281.163.) $^1H$ n.m.r. δ($CDCl_3$) 14.74, very broad s, 1H; 4.10, q, J 6 Hz, $O\underline{CH_2}CH_3$; 2.99, t, J 7.5 Hz, $\underline{CH_2}CH_2CH_3$; 2.67, broad s, 2H10; 2.3-1.15, m, 10H; 1.35, t, J 7 Hz $OCH_2\underline{CH_3}$; 0.98, t, J 7 Hz, $CH_2CH_2\underline{CH_3}$. $\nu_{max}$ (film) 1707 s. 1623 s, 1410 s, 1050 s $cm^{-1}$.

EXAMPLE 5

8-[1-(Ethoxyimino)butyl]-9-hydroxy-2-methyl-6-oxaspiro[4.5]dec-8-en-7-one (3.9) (from 3-methylcylopentanone, butyryl chloride and ethoxyamine hydrochloride) as a mobile pale yellow oil. (Found: M+H, 296.185. $C_{16}H_{25}NO_4$+H requires 296.186.) $^1H$ n.m.r. δ($CDCl_3$) 14.9, very broad s, 1H; 4.06, q, J 7 Hz, $O\underline{CH_2}CH_3$; 2.97, t, J 7.5 Hz, $\underline{CH_2}CH_2CH_3$; 2.65, broad s, 2H10; 2.4-0.7, m, 15H; 1.32, t, J 7 Hz, $OCH_2\underline{CH_3}$. $\nu_{max}$ (film) 1710 s, 1623, 1411 s, 1052 s $cm^{-1}$.

EXAMPLE 6

A 1.0:1.8 Mixture of (Z):(E) 8-[1-[(3-Chloro-2-propenyl)oxyimino)butyl]-9-hydroxy-2-methyl-6-oxaspiro[4.5]dec-8-en-7-one (3.12) (from 3-methylcyclopentanone, butyryl chloride and a mixture of (Z)- and (E)-3-chloro-2-propenyloxyamine hydrochloride) as a viscous amber oil. (Found: M+H, 342.146.

$C_{17}H_{24}ClNO_4+H$ requires 342.147.) $^1H$ n.m.r. δ($CDCl_3$) 14.20, broad s, 1H; 6.5–5.85, m, 2x=CH; 4.74, d, J 6.5 Hz, $NOCH_2$ of (Z) isomer; 4.48, d, J 6 Hz, $NOCH_2$ of (E) isomer; 2.95, t, J 7.5 Hz, $\underline{CH_2}CH_2CH_3$; 2.70, unresolved d, 2H5; 2.4–0.7, m, 15H. $\nu_{max}$ (film) 1712 s, 1623 s, 1410 s $cm^{-1}$.

EXAMPLE 7

A 1.0:2.0 Mixture of (Z):(E) 3-[1-[(3-Chloro-2-propenyl)oxyimino)butyl]-4-hydroxy-1-oxaspiro[5.6-]dodec-3-en-2-one (5.4) [from cycloheptanone, butyryl chloride and a mixture of (Z)- and (E)-3-chloro-2-propenyloxyamine hydrochloride) as a pale yellow oil which solidified on cooling (5°-10° C.) to a white waxy solid m.p. <20°-50° C. (Found: M, 355.156. $C_{18}H_{26}ClNO_4$ requires 355.155.) $^1H$ n.m.r. δ($CDCl_3$) 14.12, very broad s, 1H; 6.5–5.75, m, 2×=CH; 4.74, d, J 6 Hz, $NOCH_2$ of (Z) isomer; 4.52, d, J 6 Hz, $NOCH_2$ of (E) isomer; 2.94, broad t, J 7.5 Hz, $\underline{CH_2}CH_2CH_3$; 2.61, broad s, 2H5; 2.2–0.9, m, 14H; 0.97, t, J 7 Hz, $CH_3$. $\nu_{max}$ (nujol) 1714 s, 1622 s, 1406 s, 1378 s, 1025 s $cm^{-1}$.

EXAMPLE 8

3-[1-(Ethoxyimino)butyl]-4-hydroxy-1-oxa-9-thiaspiro[5.5]undec-3-en-2-one (6.17) (from tetrahydrothiopyran-4-one, butyryl chloride and ethoxyamine hydrochloride) as a viscous pale yellow oil. (Found: M, 313.134. $C_{15}H_{23}NO_4S$ requires 313.135.) $^1H$ n.m.r. δ($CDCl_3$) 15.0, very broad s, 1H; 4.08, q, J 7 Hz, $\underline{OCH_2}CH_3$; 3.27–2.79, m and 2.07–1.4, m, 12H; 2.57, s, 2H5; 1.35, t, J 7.5 Hz, $OCH_2\underline{CH_3}$; 1.00, t, J 7.5 Hz, $CH_2CH_2\underline{CH_3}$. $\nu_{max}$ (film) 1707 s, 1623 s, 1412 s, 1049 s $cm^{-1}$.

The compounds made using Method B (for the synthesis of the pyrandiones) include those of the following examples (9–11).

EXAMPLE 9

Preparation of 3-[1-(Ethoxyimino)butyl]-4-hydroxy-1-oxa-8,11-dithiaspiro[5.6]dodec-3-en-2-one (6.25)

(a) 1-Oxa-8,11-dithiaspiro[5.6]dodeca-2,4-dione (7.26)

1,4-Dithiacycloheptan-6-one (4.93 g, 33.3 mmol in 5 ml of tetrahydrofuran) was reacted with the dianion of methyl acetoacetate (ca. 33 mmol) as described in Method B in the general procedure above. (The ice-cold mixture was quenched with methanol 30 min after addition of the ketone.) A first crop crystallized immediately upon acidification of the final aqueous solution, and was filtered and washed with ether to give the pyrandione (7.26) (3.33 g. 43%) as off-white microgranules m.p. 174°-178° C. Mass spectrum m/z 233 (M+1).

(b) 3-Butyryl-4-hydroxy-1-oxa-8,11-dithiaspiro[5.6]dodec-3-en-2-one (8.52)

The pyrandione (7.26) (2.32 g, 10.0 mmol) was acylated with butyryl chloride (1.38 g, 13.0 mmol) in the presence of DBU, and the O-butyryl intermediate rearranged by heating with 4-dimethylaminopyridine, as described in Part (b) of the general procedure above, to afford the C-acylated compound (8.52) (1.70 g, 56%) as a pale brown oil which solidified to a beige solid m.p. 88°-93° C. Mass spectrum m/z 303 (M+1). $^1H$ n.m.r. δ($CDCl_3$) 13.8, very broad s, OH; 4.1–1.35, complex, 14H; 1.35–0.80, m, $CH_3$.

(c) 3-[1-(Ethoxyimino)butyl]-4-hydroxy-1-oxa-8,11-dithiaspiro[5.6]dodec-3-en-2-one (6.25)

The acylated compound (8.52) (0.453 g, 1.50 mmol) was oximated with ethoxyamine hydrochloride (0.195 g, 2.00 mmol) in methanol (10 ml) as described in Part (c) of the general procedure above to afford a product which was recrystallized from ether to give the title compound (6.25) (0.170 g, 33%) as white microcrystals m.p. 108°-110° C. Mass spectrum m/z 346 (M+1). $^1H$ n.m.r. δ($CDCl_3$) 4.11, q, J 7 Hz, $\underline{OCH_2}CH_3$; 3.95–1.1, complex, 14H; 1.33, t, J 7 Hz, $OCH_2\underline{CH_3}$; 1.00, t, J 7 Hz $CH_2CH_2\underline{CH_3}$.

EXAMPLE 10

8-[1-(Ethoxyimino)butyl]-9-hydroxy-6-oxa-2-thiaspiro[4.5]dec-8-en-7-one (6.1) (from tetrahydrothiophen-3-one, butyryl chloride and ethoxyamine hydrochloride using acetic acid to aid lactonization in Step (a) of the general synthetic procedure) as a viscous pale yellow oil. Mass spectrum m/z 300 (M+1). $^1H$ n.m.r. δ($CDCl_3$) 4.10, q, J 7 Hz, $\underline{OCH_2}CH_3$; 4.0–0.6, complex, 12H; 1.35, t, J 7 Hz, $OCH_2\underline{CH_3}$; 1.00, t, J 7 Hz, $CH_2CH_2\underline{CH_3}$.

EXAMPLE 11

3-[1-(Ethoxyimino)butyl]-4-hydroxy-1-oxaspiro[5.6-]dodeca-3,7-dien-2-one (5.10) (from 2-cyclohepten-1-one, butyryl chloride and ethoxyamine hydrochloride) as a viscous light yellow oil. Mass spectrum m/z 308 (M+1). $^1H$ n.m.r. δ($CDCl_3$) 6.2–5.4, m, 2×=CH; 4.06, q, J 7 Hz, $\underline{OCH_2}CH_3$; 3.3–2.55, m, 2H5 and 2H and $\underline{CH_2}CH_2CH_3$; 2.55–1.0, m, 8H; 1.33, t, J 7 Hz, $OCH_2\underline{CH_3}$; 0.98, t, J 7 Hz, $CH_2CH_2\underline{CH_3}$.

EXAMPLE 12

The pre-emergent herbicidal activities of the compounds of the invention were assessed by the following procedure:

Seeds of each of the test species were sown 5 mm deep in presterilized soil in square plastic pots approximately 6 cm×7 cm with an appropriate number of seeds per pot to avoid overcrowding and allow satisfactory plant development. The pots were then placed at randomised positions in trays 30 cm×34 cm so that each tray contained one of each test species.

The required quantity of the test compound was dissolved in acetone and the acetone solution dispersed in water to give a spray liquid volume equivalent to 1000 l/ha.

Two trays were sprayed with the test compound for each application rate using a flat fan even swathe nozzle. One tray for each ten chemical treatments was sprayed with acetone/water only and was included in the remainder of the test procedure to act as control. All the trays were placed in a glasshouse, lightly watered with an overhead spray to initiate germination and then spray irrigated as required for optimum plant growth. After three weeks the trays were removed from the greenhouse and the effect of the treatment was assessed. The assessments were on a 1-10 scale, where 0=no effect and 10=plants dead.

The test species and results are shown for the compounds of Examples 1-8 in Tables 7-14 respectively.

EXAMPLE 13

The post-emergent herbicidal activities of the compounds of the invention were assessed by the following procedure:

Seeds of each of the test species were sown 5 mm deep in presterilized soil in square plastic pots approximately 6 cm×7 cm with an appropriate number of seeds per pot to avoid overcrowding and allow satisfactory plant development. The pots were then placed at randomised positions in trays 30 cm×34 cm so that each tray contained one of each test species.

All the trays were placed in a glasshouse, lightly watered with an overhead spray to initiate germination and then spray irrigated as required for optimum plant growth. After the plants had grown to a height of 10 to 12.5 cm the required quantity of the test compound was dissolved in acetone and the acetone solution dispersed in water to give a spray liquid volume equivalent to 1000 l/ha.

Two trays were sprayed with the test compound for each application rate using a flat fan even swathe nozzle. One tray for each ten chemical treatments was sprayed with acetone/water solution only and was included in the remainder of the test procedure to act as control.

The treated trays were then returned to the greenhouse. After three weeks post-treatment the effect of the treatment was visually assessed. The assessments were on a 0-10 scale, where 0=no effect and 10=plants dead.

The test species and results are shown for the compounds of Examples 1-8 in Tables 7-14 respectively. The results demonstrate the herbicidal activity of the compounds of Formula (2) in either pre-emergent (soil treatment) or post emergent (foliar) application: they also demonstrate that the compounds of the invention are superior to the prior art compounds in their selectivity for weed grasses in broadleafed crops.

The following Example provides a further illustration of the selectivity of the compounds of Formula (2) wherein crop and weed species are planted and treated in the same container.

EXAMPLE 14

18 cm diameter plastic flower pots containing sandy loam were planted with sugarbeets and key grass weeds. Three pots were used, each containing 3-4 species at about 5 plants/species, with each species confined to a distinct area. The required quantity of test compounds was dissolved in a non-phytotoxic solvent and sprayed onto the soil surface at an application rate of 1 kg/ha. After spraying, the planted pots were immediately placed in a greenhouse.

After 30 days the pots were removed from the greenhouse and the effect of the treatment was assessed. The assessments were on a 1-10 scale, where 0=no injury and 10=plants dead. All treated plants were compared with untreated controls.

Compound 4.13 (Table 2) was compared with the compound Nortron ®(ethofumesate) sold for pre-emergence control of grasses with the following results:

| | RATING | | | | | | |
|---|---|---|---|---|---|---|---|
| COMPOUND | Sugar beet | Wheat | Wild oats | Barley | Rye grass | Black-grass | Green foxtail |
| 4.13 | 0 | 10 | 10 | 10 | 10 | 10 | 10 |
| Nortron ® | 3 | 10 | 10 | 10 | 5 | 10 | 10 |

The compound of this invention killed all grasses without harming sugar beet while Nortron damaged sugar beet and gave only partial control of rye grass.

TABLE 7

HERBICIDAL ACTIVITY OF COMPOUND (4.9)

| PLANT | MEAN HERBICIDAL RATING | | | | | |
|---|---|---|---|---|---|---|
| | PRE-EMERGENT APPLICATION RATE kg/ha | | | POST-EMERGENT APPLICATION RATE kg/ha | | |
| FAMILY - Species | 0 | 0.1 | 0.5 | 0 | 0.1 | 0.5 |
| MONOCOTYLEDONS | | | | | | |
| *GRAMINEAE* | | | | | | |
| *Echinochloa crus-galli* | 0 | 0.5 | 10 | 0 | 4 | 9.5 |
| Panicum sp. | 0 | 0 | 10 | 0.5 | 9.5 | 10 |
| *Lolium rigidum* | 0 | 1 | 9.5 | 0.5 | 4.5 | 10 |
| maize [*Zea mays*] | 0 | 2 | 8 | 0 | 1.5 | 10 |
| rice [*Oryza staiva*] | 0 | 0 | 10 | 0 | 4.5 | 8.5 |
| wheat [Triticum sp.] | 0 | 2.5 | 8.5 | 0 | 2 | 10 |
| *CYPERACEAE* | | | | | | |
| *cyperus rotundus* | 0 | 0 | 0 | 0 | 0 | 0 |
| *ALLIACEAE* | | | | | | |
| onion [*Allium cepa*] | 0 | 0 | 0 | — | — | — |
| DICOTYLEDONS | | | | | | |
| *CHENOPODIACEAE* | | | | | | |
| *Chenopodium album* | 0 | 0 | 0 | — | — | — |
| *AMARANTHACEAE* | | | | | | |
| Amaranthus sp. (weed) | — | — | — | — | — | — |
| reed beet [*Amaranthus retroflexus*] | 0 | 0 | 0 | 0 | 0 | 0 |
| *CRUCIFERAE* | | | | | | |
| rape [*Brassica napus*] | 0 | 0 | 0 | 0 | 0 | 0 |
| *LEGUMINOSAE* | | | | | | |
| soybean [*Glycine max*] | 0 | 0 | 0 | 0 | 0 | 0 |
| lucerne [*Medicago sativa*] | 0 | 0 | 0 | — | — | — |
| *MALVACEAE* | | | | | | |
| cotton [Gossypium sp.] | 0.5 | 0 | 0.5 | 0.5 | 0 | 0 |
| *SOLANACEAE* | | | | | | |
| tomato [*Lycopersicum* | 0.5 | 0 | 0 | 0 | 0 | 0 |

TABLE 7-continued

| HERBICIDAL ACTIVITY OF COMPOUND (4.9) | | | | | | |
|---|---|---|---|---|---|---|
| | MEAN HERBICIDAL RATING | | | | | |
| PLANT | PRE-EMERGENT APPLICATION RATE kg/ha | | | POST-EMERGENT APPLICATION RATE kg/ha | | |
| FAMILY - Species | 0 | 0.1 | 0.5 | 0 | 0.1 | 0.5 |
| *esculentum*] | | | | | | |
| *CURCURBITACEAE* | | | | | | |
| squash [*Curcurbita pepo*] | 0 | 0 | 0 | 0 | 0 | 0 |
| *COMPOSITAE* | | | | | | |
| sunflower [*Helianthus annus*] | 0 | 0 | 4 | 0 | 0 | 0 |
| safflower [*Carthamus tinctorius*] | 0 | 0 | 0 | 0 | 0 | 0 |

TABLE 8

| HERBICIDAL ACTIVITY OF COMPOUND (4.11) | | | | | | |
|---|---|---|---|---|---|---|
| | MEAN HERBICIDAL RATING | | | | | |
| PLANT | PRE-EMERGENT APPLICATION RATE kg/ha | | | POST-EMERGENT APPLICATION RATE kg/ha | | |
| FAMILY - Species | 0 | 0.1 | 0.5 | 0 | 0.1 | 0.5 |
| MONOCOTYLEDONS | | | | | | |
| *GRAMINEAE* | | | | | | |
| *Setaria anceps* | 1 | 8.5 | 8.5 | 0 | 6.5 | 9.5 |
| *Echinochloa crus-galli* | 1.5 | 5 | 10 | 0 | 7 | 10 |
| Panicum sp. | 0.5 | 10 | — | — | — | |
| *Lolium rigidum* | 0 | 10 | 10 | 0 | 8 | 9.5 |
| maize [*Zea mays*] | 0 | 0.5 | 3 | 0 | 3 | 10 |
| rice [*Oryza sativa*] | 0 | 0 | 2.5 | 0 | 9 | 10 |
| wheat [Triticum sp.] | 0 | 4 | 10 | 0 | 9 | 10 |
| *CYPERACEAE* | | | | | | |
| cyperus rotundus | 0 | 0 | 0 | 0 | 0 | 0 |
| *ALLIACEAE* | | | | | | |
| onion [*Allium cepa*] | 0 | 0 | 2 | — | — | — |
| DICOTYLEDONS | | | | | | |
| *CHENOPODIACEAE* | | | | | | |
| *Chenopodium album* | 0 | 2.5 | 7.5 | 0 | 5 | 8.5 |
| *AMARANTHACEAE* | | | | | | |
| Amaranthus sp. (weed) | 0 | 2.5 | 5 | 0 | 1.5 | 1.5 |
| red beet [*Amaranthus retroflexus*] | 0 | 0 | 0 | 0 | 5 | 7.5 |
| *CRUCIFERAE* | | | | | | |
| rape [*Brassica napus*] | 0 | 0 | 0 | 0 | 1.5 | 4.5 |
| *LEGUMINOSAE* | | | | | | |
| soybean [*Glycine max*] | 0 | 0 | 0 | 0 | 4 | 2 |
| lucerne [*Medicago sativa*] | 1 | 0 | 1 | — | — | — |
| *MALVACEAE* | | | | | | |
| cotton [Gossypium sp.] | 0 | 0 | 0 | 0 | 2 | 3.5 |
| *SOLANACEAE* | | | | | | |
| tomato [*Lycopersicum esculentum*] | 0 | 0 | 0 | 0 | 1 | 6.5 |
| *CUCURBITACEAE* | | | | | | |
| squash [*Cucurbita pepo*] | 0.5 | 0 | 0 | 0 | 1 | 1 |
| *COMPOSITAE* | | | | | | |
| sunflower [*Helianthus annuus*] | 1.5 | 0 | 2.5 | 0.5 | 1.5 | 0.5 |
| safflower [*Carthamus tinctorius*] | 0 | 8 | 8.5 | 0 | 2 | 3.5 |

TABLE 9

| HERBICIDAL ACTIVITY OF COMPOUND (4.19) | | | | | | |
|---|---|---|---|---|---|---|
| | MEAN HERBICIDAL RATING | | | | | |
| PLANT | PRE-EMERGENT APPLICATION RATE kg/ha | | | POST-EMERGENT APPLICATION RATE kg/ha | | |
| FAMILY - Species | 0 | 0.1 | 0.5 | 0 | 0.1 | 0.5 |
| MONOCOTYLEDONS | | | | | | |
| *GRAMINEAE* | | | | | | |
| *Setaria anceps* | 0 | 0 | 9.5 | 0 | 8.5 | 9 |
| *Echinochloa crus-galli* | 0 | 5 | 8.5 | 0 | 10 | 10 |
| Panicum sp. | 0 | 1 | 8 | — | — | — |
| *Lolium rigidum* | 0 | 1 | 7.5 | 0 | 8.5 | 9 |

TABLE 9-continued

HERBICIDAL ACTIVITY OF COMPOUND (4.19)

| PLANT FAMILY - Species | MEAN HERBICIDAL RATING PRE-EMERGENT APPLICATION RATE kg/ha 0 | 0.1 | 0.5 | POST-EMERGENT APPLICATION RATE kg/ha 0 | 0.1 | 0.5 |
|---|---|---|---|---|---|---|
| maize [*Zea mays*] | 0 | 0 | 8 | 0 | 6.5 | 10 |
| rice [*Oryza sativa*] | 0.5 | 0 | 8 | 0 | 3.5 | 9 |
| wheat [Triticum sp.] | 0 | 0 | 4.5 | 0 | 1 | 7 |
| *CYPERCEAE* | | | | | | |
| *cyperus rotundus* | 0 | 0 | 0 | 0 | 0 | 0 |
| *ALLIACEAE* | | | | | | |
| onion [*Allium cepa*] | 0 | 0 | 0 | — | — | — |
| DICOTYLEDONS | | | | | | |
| *CHENOPODIACEAE* | | | | | | |
| *Chenopodium album* | 0.5 | 0 | 3 | 0 | 0 | 0 |
| *AMARANTHACEAE* | | | | | | |
| Amaranthus sp. (weed) | 0 | 0 | 0 | 0 | 0 | 0 |
| red beet [*Amaranthus retroflexus*] | 0 | 0 | 0 | 0 | 0 | 0 |
| *CRUCIFERAE* | | | | | | |
| rape [*Brassica napus*] | 0 | 0 | 0 | 0 | 0 | 0 |
| LEGUMINOSAE | | | | | | |
| soybean [*Glycine max*] | 0 | 0 | 0 | 0 | 0 | 0 |
| lucerne [*Medicago sativa*] | 0 | 0 | 0 | — | — | — |
| *MALVACAE* | | | | | | |
| cotton [Gossypium sp.] | 0 | 0 | 0 | 0 | 0 | 0 |
| *SOLANACEAE* | | | | | | |
| tomato [*Lycopersicum esculentum*] | 0 | 0 | 0 | 0 | 0 | 0 |
| *CUCURBITACEAE* | | | | | | |
| squash [*Cucurbita pepo*] | 0 | 0 | 0 | 0 | 0 | 0 |
| *COMPOSITAE* | | | | | | |
| sunflower [*Helianthus annuus*] | 0 | 0 | 0 | 0 | 0 | 0 |
| safflower [*Carthamus tinctorius*] | 0 | 0 | 0 | 0 | 0 | 0 |

TABLE 10

HERBICIDAL ACTIVITY OF COMPOUND (3.1)

| PLANT FAMILY - Species | MEAN HERBICIDAL RATING PRE-EMERGENCT APPLICATION RATE kg/ha 0 | 0.1 | 0.5 | POST-EMERGENT APPLICATION RATE kg/ha 0 | 0.1 | 0.5 |
|---|---|---|---|---|---|---|
| MONOCOTYLEDONS | | | | | | |
| *GRAMINEAE* | | | | | | |
| *Setaria anceps* | 0 | 4 | 8.5 | 0 | 8.5 | 10 |
| *Echinochloa crus-galli* | 0.5 | 7 | 10 | 0 | 8 | 9 |
| Panicum sp. | 0 | 5.5 | 10 | 0 | 7.5 | 9 |
| *Lolium rigidum* | 0 | 5 | 10 | 0 | 8.5 | 9 |
| maize [*Zea mays*] | 0 | 9.5 | 9.5 | 0.5 | 0 | 8.5 |
| rice [*Oryza sativa*] | 0 | 0 | 0 | 0 | 1 | 6.5 |
| wheat [Triticum sp.] | 0 | 1 | 4 | 0 | 0.5 | 7.5 |
| *CYPERCEAE* | | | | | | |
| *cyperus rotundus* | 0 | 0 | 0 | 0 | 0 | 0 |
| *ALLIACEAE* | | | | | | |
| onion [*Allium cepa*] | 0 | 0 | 0 | 0 | 0 | 0 |
| DICOTYLEDONS | | | | | | |
| *CHENOPODIACEAE* | | | | | | |
| *Chenopodium album* | 0 | 0 | 0 | 0 | 0 | 0 |
| AMARANTHACEAE | | | | | | |
| Amaranthus sp. (weed) | 0 | 0 | 0 | 0 | 0 | 0 |
| red beet [*Amaranthus retroflexus*] | 0.5 | 0 | 0 | 0 | 0 | 0 |
| CRUCIFERAE | | | | | | |
| rape [*Brassica napus*] | 0 | 0 | 0 | 0 | 0 | 0 |
| *LEGUMINOSAE* | | | | | | |
| soybean [*Glycine max*] | — | — | — | 0 | 0 | 0 |
| lucerne [*Medicago sativa*] | 0 | 0 | 0 | 0 | 0 | 0 |
| *MALVACEAE* | | | | | | |
| cotton [Gossypium sp.] | 0 | 2.5 | 2 | 0 | 0 | 0 |
| *SOLANCEAE* | | | | | | |
| tomato [*Lycopersicum* | 0.5 | 0 | 0 | 0 | 0 | 0 |

TABLE 10-continued

HERBICIDAL ACTIVITY OF COMPOUND (3.1)

| PLANT FAMILY - Species | MEAN HERBICIDAL RATING PRE-EMERGENCT APPLICATION RATE kg/ha 0 | 0.1 | 0.5 | POST-EMERGENT APPLICATION RATE kg/ha 0 | 0.1 | 0.5 |
|---|---|---|---|---|---|---|
| *esculentum*] | | | | | | |
| *CUCURBITACEAE* | | | | | | |
| squash [*Cucurbita pepo*] | 0.5 | 0 | 0 | 0 | 0 | 0 |
| *COMPOSITAE* | | | | | | |
| sunflower [*Helianthus annuus*] | 0 | 0 | 0 | 0.5 | 0 | 0 |
| safflower [*Carthamus tinctorius*] | 0 | 0 | 0 | 0 | 0 | 0 |

TABLE 11

HERBICIDAL ACTIVITY OF COMPOUND (3.9)

| PLANT FAMILY - Species | MEAN HERBICIDAL RATING PRE-EMERGENT APPLICATION RATE kg/ha 0 | 0.1 | 0.5 | POST-EMERGENT APPLICATION RATE kg/ha 0 | 0.1 | 0.5 |
|---|---|---|---|---|---|---|
| MONOCOTYLEDONS | | | | | | |
| *GRAMINEAE* | | | | | | |
| *Setaria anceps* | 0 | 0 | 10 | 0 | 8 | 9 |
| *Echinocloa crus-galli* | 0 | 1.5 | 3 | 0 | 9 | 10 |
| Panicum sp. | 0 | 1 | 8.5 | — | — | — |
| *Lolium rigidum* | 0 | 0 | 6.5 | 0 | 4.5 | 9 |
| maize [*Zea mays*] | 0 | 0 | 3 | 0 | 1 | 10 |
| rice [*Oryza sativa*] | 0.5 | 0 | 6 | 0 | 0 | 7 |
| wheat [Triticum sp.] | 0 | 0 | 4 | 0 | 0 | 2 |
| *CYPERCEAE* | | | | | | |
| *cyperus rotundus* | 0 | 0 | 0 | 0 | 0 | 0 |
| *ALLIACEAE* | | | | | | |
| onion [*Allium cepa*] | 0 | 0 | 0 | — | — | — |
| DICOTYLEDONS | | | | | | |
| *CHENOPODIACEAE* | | | | | | |
| *Chenopodium album* | 0.5 | 0 | 4 | 0 | 0 | 0 |
| *AMARANTHACEAE* | | | | | | |
| Amaranthus sp. (weed) | 0 | 0 | 0 | 0 | 0 | 0 |
| red beet [*Amaranthus retroflexus*] | 0 | 0 | 0 | 0 | 0 | 0 |
| *CRUCIFERAE* | | | | | | |
| rape [*Brassica napus*] | 0 | 0 | 0 | 0 | 0 | 0 |
| *LEGUMINOSAE* | | | | | | |
| soybean [*Glycine max*] | 0 | 0 | 0 | 0 | 0 | 0 |
| lucerne [*Medicago sativa*] | 0 | 0 | 0 | — | — | — |
| *MALVACEAE* | | | | | | |
| cotton [Gossypium sp.] | 0 | 0 | 1 | 0 | 0 | 0 |
| *SOLANACEAE* | | | | | | |
| tomato [*Lycopersicum esculentum*] | 0 | 0 | 0.5 | 0 | 0 | 0 |
| *CUCURBITACEAE* | | | | | | |
| squash [*Cucurbita pepo*] | 0 | 0 | 0 | 0 | 0 | 0 |
| *COMPOSITAE* | | | | | | |
| sunflower [*Helianthus annuus*] | 0 | 0 | 0 | 0 | 0 | 0 |
| safflower [*Carthamus tinctorius*] | 0 | 0 | 3.5 | 0 | 0 | 0 |

TABLE 12

HERBICIDAL ACTIVITY OF A 1.0:1.8 MIXTURE OF (Z):(E) COMPOUND (3.12)

| PLANT FAMILY - Species | MEAN HERBICIDAL RATING PRE-EMERGENT APPLICATION RATE kg/ha 0 | 0.1 | 0.5 | POST-EMERGENT APPLICATION RATE kg/ha 0 | 0.1 | 0.5 |
|---|---|---|---|---|---|---|
| MONOCOTYLEDONS | | | | | | |
| *GRAMINEAE* | | | | | | |
| *Setaria anceps* | 0 | 3 | 9.5 | 0 | 7.5 | 10 |
| *Echinochloa crus-galli* | 0 | 1.5 | 3.5 | 0 | 7.5 | 10 |
| Panicum sp. | 0 | 2 | 6 | — | — | — |
| *Lolium rigidum* | 0 | 0 | 10 | 0 | 4 | 9.5 |

TABLE 12-continued

| HERBICIDAL ACTIVITY OF A 1.0:1.8 MIXTURE OF (Z):(E) COMPOUND (3.12) | | | | | | |
|---|---|---|---|---|---|---|
| | MEAN HERBICIDAL RATING | | | | | |
| PLANT | PRE-EMERGENT APPLICATION RATE kg/ha | | | POST-EMERGENT APPLICATION RATE kg/ha | | |
| FAMILY - Species | 0 | 0.1 | 0.5 | 0 | 0.1 | 0.5 |
| maize [*Zea mays*] | 0 | 2.5 | 4.5 | 0 | 1 | 2 |
| rice [*Oryza sativa*] | 0.5 | 1.5 | 4 | 0 | 2 | 6.5 |
| wheat [Triticum sp.] | 0 | 1 | 4 | 0 | 1 | 1.5 |
| *CYPERCEAE* | | | | | | |
| *cyperus rotundus* | 0 | 0 | 0 | 0 | 0 | 0 |
| *ALLIACEAE* | | | | | | |
| onion [*Allium cepa*] | 0 | 0 | 1.5 | — | — | — |
| DICOTYLEDONS | | | | | | |
| *CHENOPODIACEAE* | | | | | | |
| *Chenopodium album* | 0.5 | 4 | 6.5 | 0 | 0 | 0 |
| *AMARANTHACEAE* | | | | | | |
| Amaranthys sp. (weed) | 0 | 0 | 0 | 0 | 0 | 0 |
| red beet [*Amaranthus retroflexus*] | 0 | 0 | 0 | 0 | 0 | 0 |
| *CRUCIFERAE* | | | | | | |
| rape [*Brassica napus*] | 0 | 0 | 0 | 0 | 0 | 0 |
| *LEGUMINOSAE* | | | | | | |
| soybean [*Glycine max*] | 0 | 0 | 0 | 0 | 0 | 0 |
| lucerne [*Medicago sativa*] | 0 | 0 | 0 | — | — | — |
| *MALVACEAE* | | | | | | |
| cotton [Gossypium sp.] | 0 | 0 | 0 | 0 | 0 | 0 |
| *SOLANACEAE* | | | | | | |
| tomato [*Lycopersicum esculentum*] | 0 | 0 | 0 | 0 | 0 | 0 |
| *CUCURBITACEAE* | | | | | | |
| squash [*Cucurbita pepo*] | 0 | 0 | 0 | 0 | 0 | 0 |
| *COMPOSITAE* | | | | | | |
| sunflower [*Helianthus annuus*] | 0 | 0 | 0 | 0 | 0 | 0 |
| safflower [*Carthamus tinctorius*] | 0 | 0 | 0 | 0 | 0 | 0 |

TABLE 13

| HERBICIDAL ACTIVITY OF A 1.0:2.0 MIXTURE OF (Z):(E) COMPOUND (5.4) | | | | | | |
|---|---|---|---|---|---|---|
| | MEAN HERBICIDAL RATING | | | | | |
| PLANT | PRE-EMERGENT APPLICATION RATE kg/ha | | | POST-EMERGENT APPLICATION RATE kg/ha | | |
| FAMILY - Species | 0 | 0.1 | 0.5 | 0 | 0.1 | 0.5 |
| MONOCOTYLEDONS | | | | | | |
| *GRAMINEAE* | | | | | | |
| *Setaria anceps* | 0.5 | 5.5 | 10 | 0 | 0.5 | 9 |
| *Echinochloa crus-galli* | 0.5 | 2.5 | 10 | 0 | 2 | 9 |
| Panicum sp. | 0.5 | 5.5 | 10 | 0 | 1.5 | 8.5 |
| *Lolium rigidum* | 0 | 8 | 10 | 0 | 1.5 | 7 |
| maize [*Zea mays*] | 0.5 | 0 | 0 | 0 | 0 | 1 |
| rice [*Oryza sativa*] | 1 | 0 | 0 | 0 | 0 | 0 |
| wheat [Triticum sp.] | 0 | 0 | 0 | 0 | 0 | 0.5 |
| *CYPERACEAE* | | | | | | |
| *cyperus rotundus* | 0 | 0 | 0 | 0 | 0 | 0 |
| *ALLIACEAE* | | | | | | |
| onion [*Allium cepa*] | 0 | 0 | 0 | — | — | — |
| DICOTYLEDONS | | | | | | |
| *CHENOPODIACEAE* | | | | | | |
| *Chenopodium album* | 0 | 0 | 2.5 | 0 | 0 | 0 |
| AMARANTHACEAE | | | | | | |
| Amaranthus sp. (weed) | 0 | 0 | 0 | 0 | 0 | 0 |
| red beet [*Amaranthus retroflexus*] | 0 | 0 | 0 | 0 | 0 | 0 |
| *CRUCIFERAE* | | | | | | |
| rape [*Brassica napus*] | 0 | 0 | 0 | 0 | 0 | 0 |
| *LEGUMINOSAE* | | | | | | |
| soybean [*Glycine max*] | 0 | 0 | 0 | 0 | 0 | 0 |
| lucerne [*Medicago sativa*] | 0 | 0 | 0 | 0 | 0 | 0 |
| *MALVACEAE* | | | | | | |
| cotton [Gossypium sp.] | 0 | 0 | 0 | 0 | 0 | 0 |
| *SOLANACEAE* | | | | | | |
| tomato [*Lycopersicum* | 0 | 0 | 0 | 0 | 0 | 0 |

TABLE 13-continued

| HERBICIDAL ACTIVITY OF A 1.0:2.0 MIXTURE OF (Z):(E) COMPOUND (5.4) | | | | | | |
|---|---|---|---|---|---|---|
| | MEAN HERBICIDAL RATING | | | | | |
| PLANT | PRE-EMERGENT APPLICATION RATE kg/ha | | | POST-EMERGENT APPLICATION RATE kg/ha | | |
| FAMILY - Species | 0 | 0.1 | 0.5 | 0 | 0.1 | 0.5 |
| *esculentum*] | | | | | | |
| *CUCURBITACEAE* | | | | | | |
| squash [*Cucurbita pepo*] | 0 | 0 | 1 | 0 | 0 | 0 |
| *COMPOSITAE* | | | | | | |
| sunflower [*Helianthus annuus*] | 0 | 0 | 0 | 0 | 0 | 0.5 |
| safflower [*Carthamus tinctorius*] | 0.5 | 0 | 0 | — | — | — |

TABLE 14

| HERBICIDAL ACTIVITY OF COMPOUND (6.17) | | | | | | |
|---|---|---|---|---|---|---|
| | MEAN HERBICIDAL RATING | | | | | |
| PLANT | PRE-EMERGENT APPLICATION RATE kg/ha | | | POST-EMERGENT APPLICATION RATE kg/ha | | |
| FAMILY - Species | 0 | 0.1 | 0.5 | 0 | 0.1 | 0.5 |
| MONOCOTYLEDONS | | | | | | |
| *GRAMINEAE* | | | | | | |
| *Setaria anceps* | 0.5 | 0 | 10 | 0 | 10 | 10 |
| *Echinochloa crus-galli* | 1 | 1.5 | 10 | 0 | 9.5 | 10 |
| Panicum sp. | 0.5 | 0.5 | 10 | — | — | — |
| *Lolium rigidum* | 0 | 10 | 10 | 0 | 8 | 10 |
| maize [*Zea mays*] | 0 | 4.5 | 10 | 0 | 6 | 9 |
| rice [*Oryza sativa*] | 2.5 | 9 | 9.5 | 0 | 9.5 | 10 |
| wheat [Triticum sp.] | 0 | 9 | 10 | 0 | 9.5 | 9.5 |
| *CYPERCEAE* | | | | | | |
| *cyperus rotundus* | 0 | 0 | 0 | — | — | — |
| *ALLIACEAE* | | | | | | |
| onion [*Allium cepa*] | 0 | 0 | 0 | — | — | — |
| DICOTYLEDONS | | | | | | |
| *CHENOPODIACEAE* | | | | | | |
| *Chenopodium album* | 1 | 0 | 0 | 0 | 0 | 1 |
| *AMARANTHACEAE* | | | | | | |
| Amaranthus sp. (weed) | 0 | 0 | 0 | 0 | 0 | 0 |
| red beet [*Amaranthus retroflexus*] | 0 | 0 | 0 | 0 | 0 | 0 |
| *CRUCIFERAE* | | | | | | |
| rape [*Brassica napus*] | 0 | 0 | 0 | 0 | 0 | 0 |
| *LEGUMINOSAE* | | | | | | |
| soybean [*Glycine max*] | 0 | 0 | 0 | 0 | 1.5 | 0 |
| lucerne [*Medicago sativa*] | 0 | 0 | 0 | — | — | — |
| *MALVACEAE* | | | | | | |
| cotton [Gossypium sp.] | 0 | 0 | 0 | 0 | 0 | 0 |
| *SOLANACEAE* | | | | | | |
| tomato [*Lycopersicum esculentum*] | 0 | 0 | 0 | 0 | 0 | 0 |
| CUCURBITACEAE | | | | | | |
| squash [*Cucurbita pepo*] | 0 | 0 | 0 | 0 | 0 | 0 |
| *COMPOSITAE* | | | | | | |
| sunflower [*Helianthus annuus*] | 0 | 0 | 0 | 0.5 | 0 | 0 |
| safflower (*Carthamus tinctorius*] | 0 | 0 | 0 | — | — | — |

We claim:

1. A compound of the following general formula, including isomers and tautomers thereof:

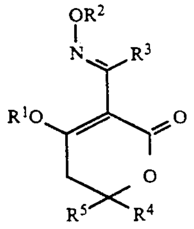

wherein:

$R^1$ is selected from the group consisting of hydrogen; optionally substituted $C_1$–$C_6$ alkyl; $C_{2-6}$ alkenyl; $C_{2-6}$ alkynyl; optionally substituted $C_{3-6}$ cycloalkyl; $C_{5-6}$ cycloalkenyl wherein the said substituted alkyl or cycloalkyl group is substituted with a substitutent selected from the group consisting of alkoxy, alkylthio and optionally substituted phenyl; optionally substituted phenyl; alkyl sulfonyl; optionally substituted benzene sulfonyl; $C_{2-6}$ acyl group; and an inorganic or organic cation;

$R^2$ is selected form the group consisting of optionally substituted $C_{1-6}$ alkyl; $C_{2-6}$ alkenyl; optionally substituted $C_{3-6}$ cycloalkyl; $C_{5-6}$ cycloalkenyl; $C_{2-6}$ haloalkenyl; $C_{2-6}$ alkynyl; $C_{2-6}$ haloalkynyl wherein the said substituted alkyl or cycloalkyl is substituted with a substituent selected from the group consisting of halogen, alkoxy, alkylthio and optionally substituted phenyl; and optionally substituted phenyl;

$R^3$ is selected from the group consisting of $C_{1-6}$ alkyl; $C_{1-6}$ haloalkyl; $C_{2-6}$ alkenyl; $C_{3-6}$ cycloalkyl; $C_{5-6}$ cycloalkenyl; $C_{2-6}$ alkynyl; and optionally substituted phenyl; wherein any carbon-containing substitutents on an $R^1$ and $R^3$ alkyl contains up to 6 carbon atoms; and $R^4$ and $R^5$ together with the carbon to which they are attached form a substituted or unsubstituted saturated or partially saturated sulfur-containing ring containing 3 to 10 ring atoms, which ring can be bridged or fused and can contain substituents selected from the group consisting of hydrogen; $C_{1-6}$ alkyl; $C_{2-6}$ alkenyl; $C_{2-6}$ alkynyl; substituted $C_{1-6}$ alkyl wherein the alkyl group is substituted with a substituent selected from the group consisting of alkoxy, alkylthio and optionally substituted phenyl; optionally substituted phenyl; oxo; $C_{2-6}$ acyl; $C_{1-6}$ alkoxy; $C_{1-6}$ alkylthio; $C_{2-6}$ alkoxycarbonyl; $C_{3-6}$ (alkoxyimino) alkyl; $C_{1-6}$ ketal; and $C_{1-6}$ carboxylic acid.

2. A compound according to claim 1:

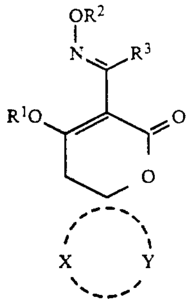

(6)

wherein: the polyatomic ring containing X and Y is a substituted or unsubstituted, saturated or partially saturated, heterocyclic ring containing 5, 6 or 7 ring atoms comprising one or more sulfur atoms and the ring substitutents are selected from the group consisting of hydrogen; $C_{1-6}$ alkyl; $C_{2-6}$ alkenyl; substituted $C_{1-6}$ alkyl wherein the alkyl group is substituted with a substituent selected from the group consisting of $C_{1-6}$ alkoxy, $C_{1-6}$ alkylthio; and optionally substituted phenyl; optionally substituted phenyl; oxo; $C_{1-6}$ acyl; $C_{1-6}$ alkoxy; $C_{1-6}$ alkylthio; $C_{1-6}$ alkoxycarbonyl; $C_{3-6}$ (alkoxyimino) alkyl; $C_{1-6}$ ketal; and $C_{1-6}$ carboxylic acid.

3. A compound according to claim 1 selected from the group:

8-[1-(Ethoxyimino)butyl]-9-hydroxy-6-oxa-2-thiaspiro[4.5]dec-8-en-7-one;

8[1-(Allyloxyimino)butyl]-9-hydroxy-6-oxa-2-thiaspiro[4.5]dec-8-en-7-one;

8-[1-[(2-Chloro-2-propenyl)oxyimino]butyl]-9-hydroxy-6-oxa-2-thiaspiro[4.5]dec-8-en-7-one;

8-[1-[(3-Chloro-2-propenyl)oxyimino]butyl]-9-hydroxy-6-oxa-2-thiaspiro[4.5]dec-8-en-7-one;

8-[1-(Ethoxyimino)propyl]-9-hydroxy-6-oxa-2-thiaspiro[4.5]dec-8-en-7-one;

8-[1-(Allyloxyimino)propyl]-9-hydroxy-6-oxa-2-thiaspiro[4.5]dec-8-en-7-one;

8-[1-[(2-Chloro-2-propenyl)oxyimino]propyl]-9-hydroxy-6-oxa-2-thiaspiro[4.5]dec-8-en-7-one;

8[1-[(3-Chloro-2-propenyl)oxyimino]propyl]-9-hydroxy-6-oxa-2-thiaspiro[4.5]dec-8-en-7-one;

3-[1-(Ethoxyimino)butyl]-4-hydroxy-1-oxa-8-thiaspiro[5.5]undec-3-en-2-one;

3-[1-(Allyloxyimino)butyl]-4-hydroxy-1-oxa-8-thiaspiro[5.5]undec-3-en-2-one;

3-[1-[(2-Chloro-2-propenyl)oxyimino]butyl]-4-hydroxy-1-oxa-8-thiaspiro[5.5]undec-3-en-2-one;

3-[1-[(3-Chloro-2-propenyl)oxyimino]butyl]-4-hydroxy-1-oxa-8-thiaspiro[5.5]undec-3-en-2-one;

3-[1-(Ethoxyimino)propyl]-4-hydroxy-1-oxa-8-thiaspiro[5.5]undec-3-en-2-one;

3-[1-(Allyloxyimino)propyl]-4-hydroxy-1-oxa-8-thiaspiro-[5.5]undec-3-en-2-one;

3-[1-[(2-Chloro-2-propenyl)oxyimino]propyl]-4-hydroxy-1-oxa-8thiaspiro[5.5]undec-3-en-2-one;

3-[1-[(3-Chloro-2-propenyl)oxyimino]propyl]-4-hydroxy-1-oxa-8-thiaspiro[5.5]undec-3-en-2-one;

3-[1-(Ethoxyimino)butyl]-4-hydroxy-1-oxa-9-thiaspiro[5.5]undec-3-en-2-one;

3-[1-(Allyloxyimino)butyl]-4-hydroxy-1-oxa-9-thiaspiro[5.5]undec-3-en-2-one;

3-[1-[(2-Chloro-2-propenyl)oxyimino]butyl]-4-hydroxy-1-oxa-9-thiaspiro[5.5]undec-3-en-2-one;

3-[1-[(3-Chloro-2-propenyl)oxyimino]butyl]-4-hydroxy-1-oxa-9-thiaspiro[5.5]undec-3-en-2-one;

3-[1-(Ethoxyimino)propyl-4-hydroxy-1-oxa-9-thiaspiro[5.5]undec-3-en-2-one;

3-[1-(Allyloxyimino)propyl]-4-hydroxy-1-oxa-9-thiaspiro-[5.5]undec-3-en-2-one;

3-[1-[(2-Chloro-2-propenyl)oxyimino]propyl]-4-hydroxy-1-oxa-9-thiaspiro[5.5]undec-3-en-2-one;

3-[1-[(3-Chloro-2-propenyl)oxyimino]propyl]-4-hydroxy-1-oxa-9-thiaspiro[5.5]undec-3-en-2-one;

3-[1-(Ethoxyimino)butyl]-4-hydroxy-1-oxa-8-dithiaspiro[5.6]dodec-3-en-2-one;

3-[1-(Allyloxyimino)butyl]-4-hydroxy-1-oxa-8,11-dithiaspiro[5.6]dodec-3-en-2-one;

3-[1-[(2-Chloro-2-propenyl)oxyimino]butyl]-4-hydroxy-1-oxa-8,11-dithiaspiro[5.6]dodec-3-en-2-one;

3-[1-[(3-Chloro-2-propenyl)oxyimino]butyl]-4-hydroxy-1-oxa-8,11-dithiaspiro[5.6]dodec-3-en-2-one;

3-[1-(Ethoxyimino)propyl]-4-hydroxy-1-oxa-8,11-dithiaspiro[5.6]dodec-3-en-2-one;

3-[1-(Allyloxyimino)propyl]-4-hydroxy-1-oxa-8,11-dithiaspiro[5.6]dodec-3-en-2-one;

3-[1-[(2-Chloro-2-propenyl)oxyimino]propyl]-4-hydroxy-1-oxa-8,11-dithiaspiro[5.6]dodec-3-en-2-one; and 3-[1-[(3-Chloro-2-propenyl)oxyimino]propyl]-4-hydroxy-1-oxa-8,11-dithiaspiro[5.6]dodec-3-en-2-one.

4. A compound as claimed in one of claims 1 and 2, wherein $R^1$ is hydrogen or an alkali metal cation.

5. A compound as claimed in one of claims 1 and 2, wherein $R^2$ is ethyl, allyl, 2-chloroallyl or 3-chloroallyl.

6. A compound as claimed in one of claims 1 and 2, wherein $R^3$ is ethyl or n-propyl.

7. A compound as claimed in claim 2 wherein the substituents on the polyatomic chain XY in formula (6) are, independently, hydrogen or methyl.

8. A plant growth inhibiting, plant damaging, or plant killing composition comprising a compound according to claim 1 and an inert carrier therefor.

9. A method for regulating the growth of a plant which process comprises applying to the plant, to the seed of the plant, or to the growth medium of the plant, an effective amount of a compound according to claim 1.

10. A method for selectively inhibiting, damaging or killing weed grasses in a broadleaf crop which comprises applying to the crop or its locus an effective amount of a compound according to claim 1.

11. A plant growth regulating composition comprising a compound according to claim 1 and an inert carrier therefor.

* * * * *